(12) United States Patent
Bolea et al.

(10) Patent No.: US 10,052,484 B2
(45) Date of Patent: Aug. 21, 2018

(54) DEVICES AND METHODS FOR SLEEP APNEA TREATMENT

(71) Applicant: Cyberonics, Inc., Houston, TX (US)

(72) Inventors: Stephen Bolea, Watertown, MN (US); Wondimeneh Tesfayesus, St. Paul, MN (US); John Beck, Prior Lake, MN (US); Thomas Hoegh, Edina, MN (US); Robert Atkinson, Lake Elmo, MN (US); Sidney Hauschild, Cottage Grove, MN (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 15/701,253

(22) Filed: Sep. 11, 2017

(65) Prior Publication Data

US 2017/0368341 A1 Dec. 28, 2017

Related U.S. Application Data

(60) Division of application No. 14/937,482, filed on Nov. 10, 2015, now Pat. No. 9,757,564, which is a
(Continued)

(51) Int. Cl.
*A61N 1/36* (2006.01)
*A61F 5/56* (2006.01)
*A61B 17/24* (2006.01)

(52) U.S. Cl.
CPC ............ *A61N 1/3611* (2013.01); *A61F 5/566* (2013.01); *A61N 1/3601* (2013.01); *A61B 2017/248* (2013.01)

(58) Field of Classification Search
CPC ..... A61N 1/3611; A61N 1/3601; A61F 5/566; A61B 2017/248
(Continued)

(56) References Cited

U.S. PATENT DOCUMENTS

| 758,030 A | 4/1904 | Carence |
|---|---|---|
| 1,520,930 A | 12/1924 | Calhoun |

(Continued)

FOREIGN PATENT DOCUMENTS

| EP | 0 900 102 B1 | 7/2004 |
|---|---|---|
| EP | 0 892 926 B1 | 6/2006 |

(Continued)

OTHER PUBLICATIONS

Aziz, L. and Ejnell, H. "Obstructive Sleep Apnea Caused by Bilateral Vocal Fold Paralysis." Ear Nose Throat J. Apr. 2003; 82(4): 326-7. Abstract.
(Continued)

*Primary Examiner* — Carl H Layno
*Assistant Examiner* — Erin M Piateski
(74) *Attorney, Agent, or Firm* — Foley & Lardner LLP

(57) ABSTRACT

Devices and methods for improving the coupling between the soft palate and the genioglossus. This may be accomplished, for example, but shortening or stiffening the palatoglossal arch. Improved coupling between the soft palate and the genioglossus may be beneficial to a patient suffering from obstructive sleep apnea (OSA) as a stand-alone procedure, or in combination procedures and devices that cause anterior displacement of the tongue such as hypoglossal nerve stimulation, genioglossus advancement surgery, mandibular advancement surgery, mandibular advancement (oral) appliances, etc.

20 Claims, 17 Drawing Sheets

Related U.S. Application Data continuation of application No. 13/633,670, filed on Oct. 2, 2012, now Pat. No. 9,205,262.

(60) Provisional application No. 61/542,617, filed on Oct. 3, 2011.

(58) Field of Classification Search
USPC .......................................................... 607/42
See application file for complete search history.

(56) References Cited

U.S. PATENT DOCUMENTS

| | | |
|---|---|---|
| 1,701,277 A | 2/1929 | Shindel |
| 1,914,418 A | 6/1933 | Goyena |
| 2,046,664 A | 7/1936 | Weaver |
| 2,151,227 A | 3/1939 | Pawelek |
| 2,237,954 A | 4/1941 | Wilsom |
| 2,243,360 A | 5/1941 | Slatis et al. |
| 2,274,886 A | 3/1942 | Carroll |
| 2,526,586 A | 10/1950 | Shuff |
| 2,693,799 A | 11/1954 | Herman, Jr. |
| 2,777,442 A | 1/1957 | Zelano |
| 2,928,388 A | 3/1960 | Jaroslaw |
| 3,292,703 A | 12/1966 | Weber |
| 3,457,917 A | 7/1969 | Mercurio |
| 3,513,839 A | 5/1970 | Vacante |
| 3,680,555 A | 8/1972 | Warncke |
| 3,722,509 A | 3/1973 | Nebel |
| 3,774,618 A | 11/1973 | Avery |
| 3,865,106 A | 2/1975 | Palush |
| 3,884,223 A | 5/1975 | Keindl |
| 3,893,463 A | 7/1975 | Williams |
| 3,906,936 A | 9/1975 | Habal |
| 4,160,252 A | 7/1979 | Lucas et al. |
| 4,160,255 A | 7/1979 | Kobayashi |
| 4,178,524 A | 12/1979 | Ritter |
| 4,200,440 A | 4/1980 | Renko |
| 4,220,150 A | 9/1980 | King |
| 4,221,217 A | 9/1980 | Amezcua |
| 4,225,034 A | 9/1980 | Sarovich |
| 4,239,918 A | 12/1980 | Keeley |
| 4,242,987 A | 1/1981 | Viessmann |
| 4,267,831 A | 5/1981 | Aguilar |
| 4,283,867 A | 8/1981 | Brown |
| 4,302,951 A | 12/1981 | Fall et al. |
| 4,313,442 A | 2/1982 | Knudson et al. |
| 4,346,398 A | 8/1982 | Lai |
| 4,374,527 A | 2/1983 | Iversen |
| 4,414,986 A | 11/1983 | Dickhudt et al. |
| 4,506,666 A | 3/1985 | Durkan |
| 4,567,892 A | 2/1986 | Plicchi et al. |
| 4,573,481 A | 3/1986 | Bullara |
| 4,602,624 A | 7/1986 | Naples et al. |
| 4,612,934 A | 9/1986 | Borkan |
| 4,777,963 A | 10/1988 | McKenna |
| 4,830,008 A | 5/1989 | Meer |
| 4,899,749 A | 2/1990 | Laroco |
| 4,899,750 A | 2/1990 | Ekwall |
| 4,915,105 A | 4/1990 | Lee |
| 4,919,136 A | 4/1990 | Alt |
| 4,934,368 A | 6/1990 | Lynch |
| 4,940,065 A | 7/1990 | Tanagho et al. |
| 4,960,133 A | 10/1990 | Hewson |
| 4,979,511 A | 12/1990 | Terry, Jr. |
| 4,996,983 A | 3/1991 | Amrhein |
| 5,016,808 A | 5/1991 | Heil et al. |
| 5,036,862 A | 8/1991 | Pohndorf |
| 5,095,905 A | 3/1992 | Klepinski |
| 5,105,826 A | 4/1992 | Smits et al. |
| 5,121,754 A | 6/1992 | Mullett |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,277,193 A | 1/1994 | Takishima et al. |
| 5,281,219 A | 1/1994 | Kallok |
| 5,282,468 A | 2/1994 | Klepinski |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,487,756 A | 1/1996 | Kallesoe et al. |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,731 A | 7/1996 | Testerman |
| 5,540,732 A | 7/1996 | Testerman |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,568,808 A | 10/1996 | Rimkus |
| 5,591,216 A | 1/1997 | Testerman et al. |
| 5,630,411 A | 5/1997 | Holscher |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,787,884 A | 8/1998 | Tovey |
| 5,826,579 A | 10/1998 | Remmers et al. |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,919,220 A | 7/1999 | Stieglitz et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard et al. |
| 6,051,052 A | 4/2000 | Monereau et al. |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pantaleo |
| 6,126,611 A | 10/2000 | Bourgeois et al. |
| 6,132,384 A | 10/2000 | Christopherson et al. |
| 6,198,970 B1 | 3/2001 | Freed et al. |
| 6,201,994 B1 | 3/2001 | Warman et al. |
| 6,205,360 B1 | 3/2001 | Carter et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,269,703 B1 | 8/2001 | Bowers |
| 6,292,703 B1 | 9/2001 | Meier et al. |
| 6,345,202 B2 | 2/2002 | Richmond et al. |
| 6,366,815 B1 | 4/2002 | Haugland et al. |
| 6,460,539 B1 | 10/2002 | Japuntich et al. |
| 6,484,725 B1 | 11/2002 | Chi |
| 6,511,458 B2 | 1/2003 | Milo et al. |

(56) References Cited

U.S. PATENT DOCUMENTS

| | | |
|---|---|---|
| 6,514,217 B1 | 2/2003 | Selmon et al. |
| 6,542,776 B1 | 4/2003 | Gordon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,609,031 B1 | 8/2003 | Law et al. |
| 6,626,179 B1 | 9/2003 | Pedley |
| 6,636,767 B1 | 10/2003 | Knudson et al. |
| 6,641,542 B2 | 11/2003 | Cho et al. |
| 6,647,289 B2 | 11/2003 | Prutchi |
| 6,651,652 B1 | 11/2003 | Ward |
| 6,718,982 B2 | 4/2004 | Smith et al. |
| 6,719,725 B2 | 4/2004 | Milo et al. |
| 6,721,603 B2 | 4/2004 | Zabara et al. |
| 6,772,015 B2 | 8/2004 | Dahl et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,876,885 B2 | 4/2005 | Swoyer et al. |
| 6,881,192 B1 | 4/2005 | Park |
| 6,883,518 B2 | 4/2005 | Mittelstadt et al. |
| 6,890,306 B2 | 5/2005 | Poezevera |
| 6,904,320 B2 | 7/2005 | Park et al. |
| 6,907,295 B2 | 7/2005 | Gross et al. |
| 6,928,324 B2 | 8/2005 | Park et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,082,331 B1 | 7/2006 | Park et al. |
| 7,087,053 B2 | 8/2006 | Vanney |
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thach et al. |
| 7,142,919 B2 | 11/2006 | Hine et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho et al. |
| 7,160,255 B2 | 1/2007 | Saadat |
| 7,178,524 B2 | 2/2007 | Noble |
| 7,200,440 B2 | 4/2007 | Kim et al. |
| 7,225,034 B2 | 5/2007 | Ries et al. |
| 7,239,320 B1 | 7/2007 | Hall et al. |
| 7,239,918 B2 | 7/2007 | Strother et al. |
| 7,239,920 B1 | 7/2007 | Thacker et al. |
| 7,242,987 B2 | 7/2007 | Holleman et al. |
| 7,263,996 B2 | 9/2007 | Yung Ho |
| 7,277,749 B2 | 10/2007 | Gordon et al. |
| 7,283,867 B2 | 10/2007 | Strother et al. |
| 7,302,951 B2 | 12/2007 | Mittelstadt et al. |
| 7,313,442 B2 | 12/2007 | Velasco et al. |
| 7,343,202 B2 | 3/2008 | Marva et al. |
| 7,346,398 B2 | 3/2008 | Gross et al. |
| 7,366,572 B2 | 4/2008 | Heruth et al. |
| 7,396,333 B2 | 7/2008 | Stahmann et al. |
| 7,438,686 B2 | 10/2008 | Cho et al. |
| 7,453,928 B2 | 11/2008 | Ten et al. |
| 7,463,928 B2 | 12/2008 | Lee et al. |
| 7,473,227 B2 | 1/2009 | Hsu et al. |
| 7,515,968 B2 | 4/2009 | Metzler et al. |
| 7,524,292 B2 | 4/2009 | Cho et al. |
| 7,561,922 B2 | 7/2009 | Cohen et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,627,375 B2 | 12/2009 | Bardy et al. |
| 7,630,771 B2 | 12/2009 | Cauller |
| 7,634,315 B2 | 12/2009 | Cholette |
| 7,636,602 B2 | 12/2009 | Baru Fassio et al. |
| 7,657,311 B2 | 2/2010 | Bardy et al. |
| 7,660,632 B2 | 2/2010 | Kirby et al. |
| 7,662,105 B2 | 2/2010 | Hatlestad |
| 7,672,728 B2 | 3/2010 | Libbus et al. |
| 7,672,729 B2 | 3/2010 | Koh et al. |
| 7,680,537 B2 | 3/2010 | Stahmann et al. |
| 7,680,538 B2 | 3/2010 | Durand et al. |
| 7,684,869 B2 | 3/2010 | Bradley et al. |
| 7,697,968 B2 | 4/2010 | Moore |
| 7,697,984 B2 | 4/2010 | Hill et al. |
| 7,697,990 B2 | 4/2010 | Ujhazy et al. |
| 7,717,848 B2 | 5/2010 | Heruth et al. |
| 7,720,534 B2 | 5/2010 | Bardy et al. |
| 7,725,195 B2 | 5/2010 | Lima et al. |
| 7,725,198 B2 | 5/2010 | Cross et al. |
| 7,734,340 B2 | 6/2010 | De Ridder |
| 7,734,348 B2 | 6/2010 | Zhang et al. |
| 7,738,952 B2 | 6/2010 | Yun et al. |
| 7,747,323 B2 | 6/2010 | Libbus et al. |
| 7,751,880 B1 | 7/2010 | Cholette |
| 7,751,885 B2 | 7/2010 | Bardy et al. |
| 7,758,384 B2 | 7/2010 | Alexander et al. |
| 7,765,000 B2 | 7/2010 | Zhang et al. |
| 7,769,461 B2 | 8/2010 | Whitehurst et al. |
| 7,783,353 B2 | 8/2010 | Libbus et al. |
| 7,785,262 B2 | 8/2010 | Melker et al. |
| 7,787,959 B1 | 8/2010 | Morgan |
| 7,792,590 B1 | 9/2010 | Pianca et al. |
| 7,797,050 B2 | 9/2010 | Libbus et al. |
| 7,797,057 B2 | 9/2010 | Harris |
| 7,797,058 B2 | 9/2010 | Mrva et al. |
| 7,805,195 B2 | 9/2010 | Zealear |
| 7,809,442 B2 | 10/2010 | Bolea et al. |
| 7,813,797 B2 | 10/2010 | Bardy et al. |
| 7,813,802 B2 | 10/2010 | Tcheng et al. |
| 7,813,809 B2 | 10/2010 | Strother et al. |
| 7,818,063 B2 | 10/2010 | Wallace et al. |
| 7,822,486 B2 | 10/2010 | Foster et al. |
| 7,860,570 B2 | 12/2010 | Whitehurst et al. |
| 7,979,128 B2 | 7/2011 | Tehrani et al. |
| 8,221,049 B1 | 7/2012 | Westendorf et al. |
| 8,249,723 B2 | 8/2012 | McCreery |
| 8,311,645 B2 | 11/2012 | Bolea et al. |
| 8,386,046 B2 | 2/2013 | Tesfayesus et al. |
| 8,428,727 B2 | 4/2013 | Bolea et al. |
| 8,498,712 B2 | 7/2013 | Bolea et al. |
| 8,626,304 B2 | 1/2014 | Bolea et al. |
| 8,639,354 B2 | 1/2014 | Bolea et al. |
| 8,718,783 B2 | 5/2014 | Bolea et al. |
| 8,744,584 B2 | 6/2014 | Camps et al. |
| 8,744,589 B2 | 6/2014 | Bolea et al. |
| 8,855,771 B2 | 10/2014 | Tesfayesus et al. |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross, Jr. |
| 2002/0156507 A1 | 10/2002 | Lindenthaler |
| 2002/0165462 A1 | 11/2002 | Westbrook et al. |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0078643 A1 | 4/2003 | Schulman et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114895 A1 | 6/2003 | Gordon et al. |
| 2003/0114905 A1 | 6/2003 | Kuzma |
| 2003/0153953 A1 | 8/2003 | Park et al. |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |

(56) References Cited

U.S. PATENT DOCUMENTS

| | | |
|---|---|---|
| 2004/0020489 A1 | 2/2004 | Gillespie et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0111139 A1 | 6/2004 | McCreery |
| 2004/0116819 A1 | 6/2004 | Alt |
| 2004/0116978 A1 | 6/2004 | Bradley |
| 2004/0138581 A1 | 7/2004 | Frei et al. |
| 2004/0153127 A1 | 8/2004 | Gordon et al. |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0215290 A1 | 10/2004 | Zealear |
| 2004/0230278 A1 | 11/2004 | Dahl et al. |
| 2004/0233058 A1 | 11/2004 | Dodds |
| 2004/0260310 A1 | 12/2004 | Harris |
| 2004/0261791 A1 | 12/2004 | Horian |
| 2005/0004610 A1 | 1/2005 | Kim et al. |
| 2005/0004810 A1 | 1/2005 | Tanaka |
| 2005/0010265 A1 | 1/2005 | Baru Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0139216 A1 | 6/2005 | Mittelstadt et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Stroether et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0005842 A1 | 1/2006 | Rashad et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0041295 A1 | 2/2006 | Osypka |
| 2006/0052836 A1 | 3/2006 | Kim et al. |
| 2006/0058588 A1 | 3/2006 | Zdeblick |
| 2006/0058852 A1 | 3/2006 | Koh et al. |
| 2006/0064029 A1 | 3/2006 | Arad (Abboud) |
| 2006/0064138 A1 | 3/2006 | Velasco et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0149334 A1 | 7/2006 | Tehrani et al. |
| 2006/0149345 A1 | 7/2006 | Boggs et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0211951 A1 | 9/2006 | Milijasevic et al. |
| 2006/0224209 A1 | 10/2006 | Meyer |
| 2006/0224211 A1* | 10/2006 | Durand ............. A61N 1/3601 607/48 |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0043411 A1 | 2/2007 | Foster et al. |
| 2007/0095347 A1 | 5/2007 | Lampotang et al. |
| 2007/0150006 A1 | 6/2007 | Libbus et al. |
| 2007/0125379 A1 | 7/2007 | Pierro et al. |
| 2007/0175478 A1 | 8/2007 | Brunst |
| 2007/0227542 A1 | 10/2007 | Kashmakov et al. |
| 2007/0239243 A1 | 10/2007 | Moffitt et al. |
| 2007/0277832 A1 | 12/2007 | Doshi et al. |
| 2007/0282410 A1 | 12/2007 | Cross et al. |
| 2007/0283692 A1 | 12/2007 | Tetsuka et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0027480 A1 | 1/2008 | Van Der Burg et al. |
| 2008/0027502 A1 | 1/2008 | Ransom |
| 2008/0041373 A1 | 2/2008 | Doshi et al. |
| 2008/0099029 A1 | 5/2008 | Lamberg |
| 2008/0103407 A1 | 5/2008 | Bolea et al. |
| 2008/0103545 A1* | 5/2008 | Bolea ................. A61N 1/0556 607/42 |
| 2008/0147142 A1 | 6/2008 | Testerman et al. |
| 2008/0163875 A1 | 7/2008 | Aarestad et al. |
| 2008/0183254 A1 | 7/2008 | Bly et al. |
| 2008/0188947 A1 | 8/2008 | Sanders |
| 2009/0044814 A1* | 2/2009 | Iancea ............. A61B 17/06109 128/848 |
| 2009/0270707 A1 | 10/2009 | Alfoqaha et al. |
| 2009/0276024 A1 | 11/2009 | Bonde et al. |
| 2009/0308395 A1 | 12/2009 | Lee et al. |
| 2009/0318986 A1 | 12/2009 | Alo et al. |
| 2009/0326408 A1 | 12/2009 | Moon |
| 2010/0016749 A1 | 1/2010 | Atsma et al. |
| 2010/0036285 A1 | 2/2010 | Govari et al. |
| 2010/0047376 A1 | 2/2010 | Imbeau et al. |
| 2010/0076536 A1 | 3/2010 | Merz et al. |
| 2010/0094379 A1 | 4/2010 | Meadows et al. |
| 2010/0100150 A1 | 4/2010 | Kirby et al. |
| 2010/0125310 A1 | 5/2010 | Wilson et al. |
| 2010/0131029 A1 | 5/2010 | Durand et al. |
| 2010/0137931 A1 | 6/2010 | Hopper et al. |
| 2010/0137949 A1 | 6/2010 | Mazgalev et al. |
| 2010/0137956 A1 | 6/2010 | Osypka |
| 2010/0152553 A1 | 6/2010 | Ujhazy et al. |
| 2010/0174341 A1 | 7/2010 | Bolea et al. |
| 2010/0228133 A1 | 9/2010 | Averina et al. |
| 2010/0228317 A1 | 9/2010 | Libbus et al. |
| 2010/0241207 A1 | 9/2010 | Bluger |
| 2010/0257729 A1 | 10/2010 | Alexander et al. |
| 2010/0262209 A1 | 10/2010 | King et al. |
| 2011/0071591 A1 | 3/2011 | Bolea et al. |
| 2011/0093032 A1 | 4/2011 | Boggs et al. |
| 2012/0017920 A1 | 1/2012 | Sanders |
| 2012/0022389 A1 | 1/2012 | Sanders |
| 2012/0192874 A1 | 8/2012 | Bolea et al. |
| 2013/0085546 A1 | 4/2013 | Bolea et al. |

FOREIGN PATENT DOCUMENTS

| | | |
|---|---|---|
| EP | 1 404 221 B1 | 2/2007 |
| EP | 1 854 494 A1 | 11/2007 |

(56) References Cited

FOREIGN PATENT DOCUMENTS

| | | |
|---|---|---|
| EP | 1 322 384 B1 | 12/2007 |
| JP | 53-118893 A | 10/1978 |
| JP | 09-294819 A | 11/1997 |
| JP | 2000-508601 | 5/2000 |
| JP | 2000-508562 A | 7/2000 |
| JP | 2003-305135 A | 10/2003 |
| JP | 2004-508908 A | 3/2004 |
| JP | 2004-532707 A | 10/2004 |
| JP | 3688301 B2 | 6/2005 |
| JP | 2005-521485 A | 7/2005 |
| JP | 2007-021156 A | 2/2007 |
| JP | 2007-021158 | 2/2007 |
| WO | WO-98/20938 A1 | 5/1998 |
| WO | WO-02/24279 A1 | 3/2002 |
| WO | WO-03/000133 A1 | 1/2003 |
| WO | WO-03/000347 A1 | 1/2003 |
| WO | WO-03/082393 A1 | 10/2003 |
| WO | WO-2005/004993 A1 | 1/2005 |
| WO | WO-2006/045251 A1 | 5/2006 |
| WO | WO-2006/063339 A2 | 6/2006 |
| WO | WO-2007/134458 A1 | 11/2007 |
| WO | WO-2008/046190 A1 | 4/2008 |

OTHER PUBLICATIONS

Campbell et al., "Nasal Continuous positive airway pressure from high flow cannula versus Infant Flow for preterm infants," Journal of Perinatology, Jul. 2006, pp. 546-549, vol. 26 (9), Nature Publishing Group.

De Almeida et al., "Nasal pressure recordings to detect obstructive sleep apnea," Sleep and Breathing, Feb. 25, 2006, pp. 62-69, vol. 10 (2), Springer Heidelberg.

Eastwood et al., "Treating Obstructive Sleep Apnea with Hypoglossal Nerve Stimulation," Sleep, 2011, pp. 1479-1486B, vol. 34, No. 11.

Ferguson et al., "Effect of Mandibular and Tongue Protrusion on Upper Airway Size During Wakefulness," American Journal of Respiratory and Critical Care Medicine, 1997, pp. 1748-1754, vol. 1553.

Goding JR et al., "Relief of Upper Airway Obstruction With Hypoglossal Nerve Stimulation in the Canine", TheLaryngoscope, Feb. 1998, pp. 162-169, vol. 108, Lippincott-Raven Publishers, U.S.A.

Huang et al. "Dilation of the oropharynx via selective stimulation of the hypoglossal nerve." J. Neural Eng. 2005; 2:73-80.

Isono et al., "Interaction of cross-sectional area, driving pressure, and airflow of passive velopharynx," American Physiological Society, 1997, pp. 851-859, vol. 83.

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

Mahadevia et al., "Effects of expiratory positive airway pressure on sleep-induced respiratory abnormalities in patients with hypersomnia-sleep apnea syndrome," Am. Rev. Respir. Cis., Feb. 1983, vol. 128, pp. 708-711.

Mann EA, et al., "The Effect of Neuromuscular Stimulation of the Genioglossus on the Hypopharyngeal Airway." Laryngoscope 112: 351-356, 2002.

Noseda et al., "Compliance with nasal continuous positive airway pressure assessed with a pressure monitor: pattern of use and influence of sleep habits," Chest Clinics and Sleep Laboratories, Hopitaux Erasme et Brugmann, Universite Libre de Bruxelles, Brussels, Belgium, 2000, vol. 94, pp. 76-81.

Oliven et al., "Effect of genioglossus contraction on pharyngeal lumen and airflow in sleep apnoea patients," European Respiratory Journal, 2007, pp. 748-758, vol. 30, No. 4.

Paquereau et al., "Positive pressure titration in the treatment of obstructive sleep apnea syndrome using continuous airway positive pressure," Revue Des Maladies Respiratoires, Apr. 2000, pp. 459-465, vol. 17 (2), Masson Editeur.

Sahin et al., "Chronic recordings of hypoglossal nerve activity in a dog model of upper airway obstruction,"Journal of Applied Physiology 87(6), 1999, The American Physiological Society, pp. 2197-2206.

Saslow et al., "Work of breathing using high-flow nasal cannula in preterm infants," Journal of Perinatology, May 11, 2006, pp. 476-480, vol. 26 (8), Nature Publishing Group.

Schwartz et al. "Therapeutic Electrical Stimulation of the Hypoglossal Nerve in Obstructive Sleep Apnea." Arch Otolaryngol Head Neck Surg/vol. 127, Oct. 2001 (8 pages).

Spence et al., "High-flow nasal cannula as a device to provide continuous positive airway pressure in infants," Journal of Perinatolgy, Dec. 2007, pp. 772-775, vol. 27 (12), Nature Publishing Group.

Stern et al. "Obstructive sleep apnea following treatment of head and neck cancer", Ear, Nose, and Throat Journal, Feb. 2007, vol. 86, No. 2, pp. 101-103.

Strollo et al., "Upper-Airway Stimulation for Obstructive Sleep Apnea," New England Journal of Medicine, 2014, pp. 139-149, N Engl J. Med 270;2.

Tiran et al., "An Improved Device for Posterior Rhinomanometry to Measure Nasal Resistance," Journal of Biomechnical Engineering, Nov. 2005, vol. 127, pp. 994-997.

Trevisanuto et al., "A new device for administration of continuous positive airway pressure in preterm infants: comparison with a standard nasal CPAP continuous positive airway pressure system," Intensive Care Medicine, Apr. 2005, pp. 859-864, vol. 31 (6), Springer-Verlag.

Verse et al., "New developments in the therapy of obstructive sleep apnea," European Archives of Oto-Rhino-Laryngology, Jan. 2001, pp. 31-37, vol. 258 (1), Springer-Verlag.

Wells, Jonathan, et al., Biophysical Mechanisms of Transient Optical Stimulation of Peripheral Nerve, Biophysical Journal, Oct. 2007, pp. 2567-2580, vol. 93.

\* cited by examiner

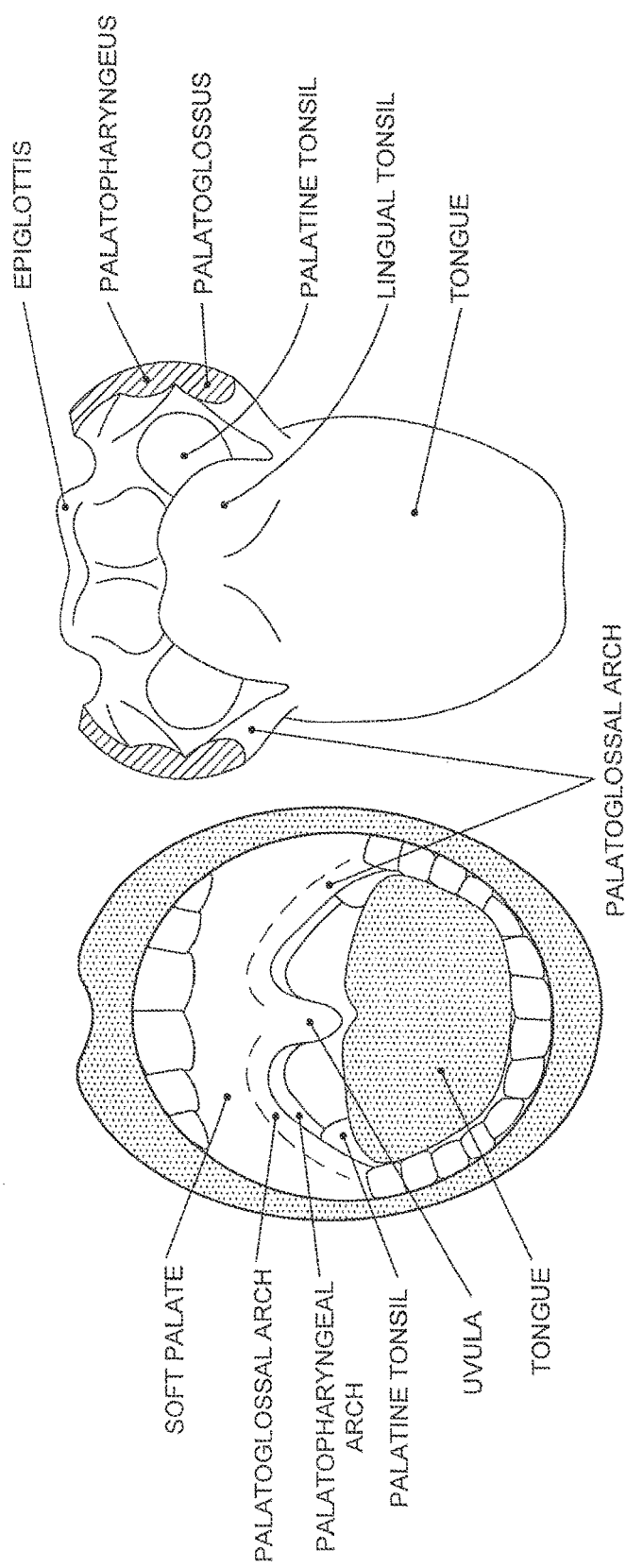

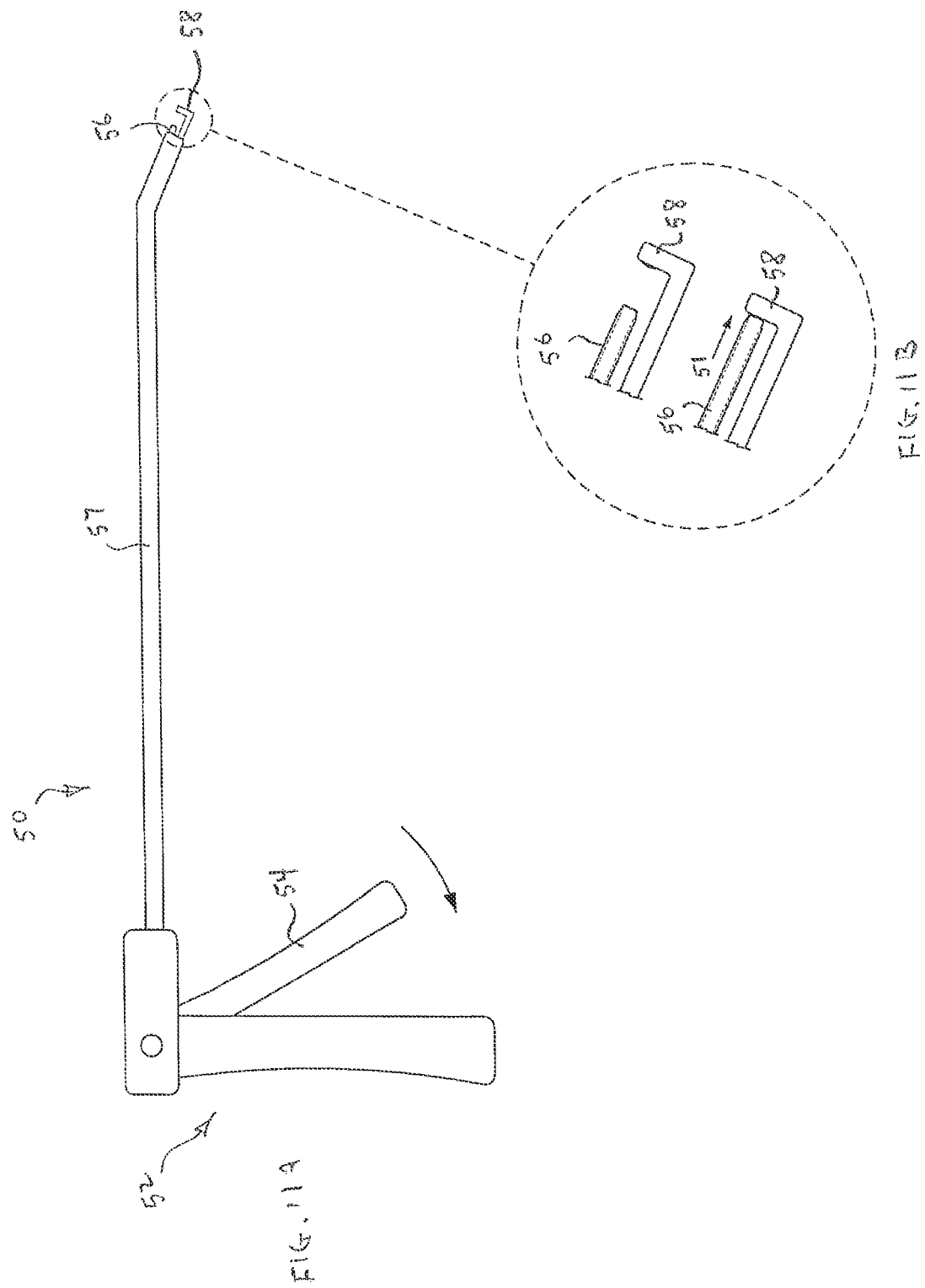

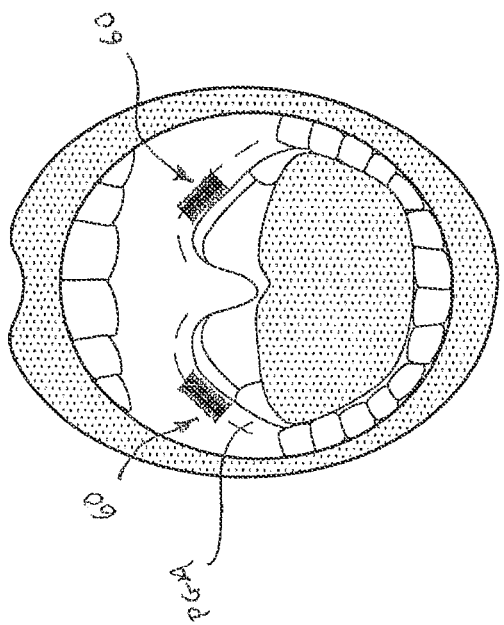
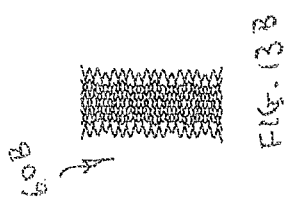
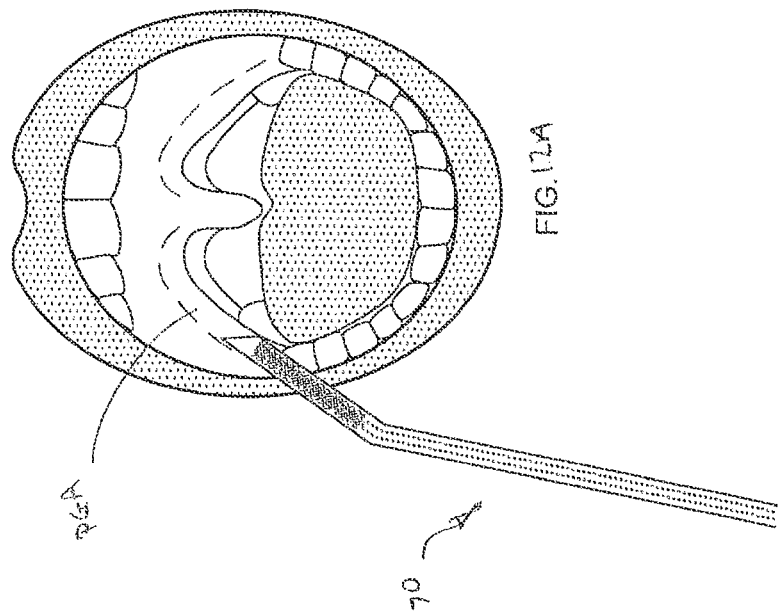

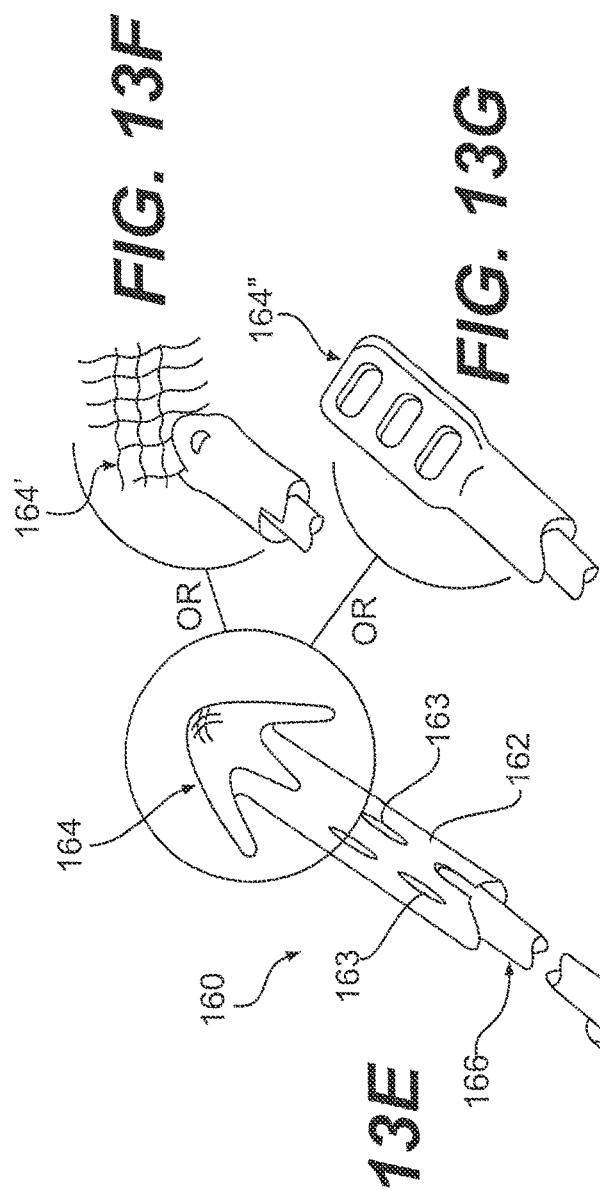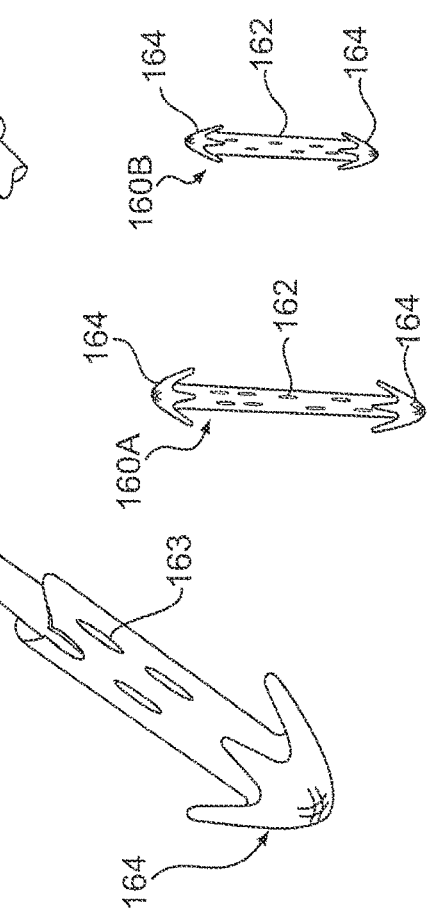

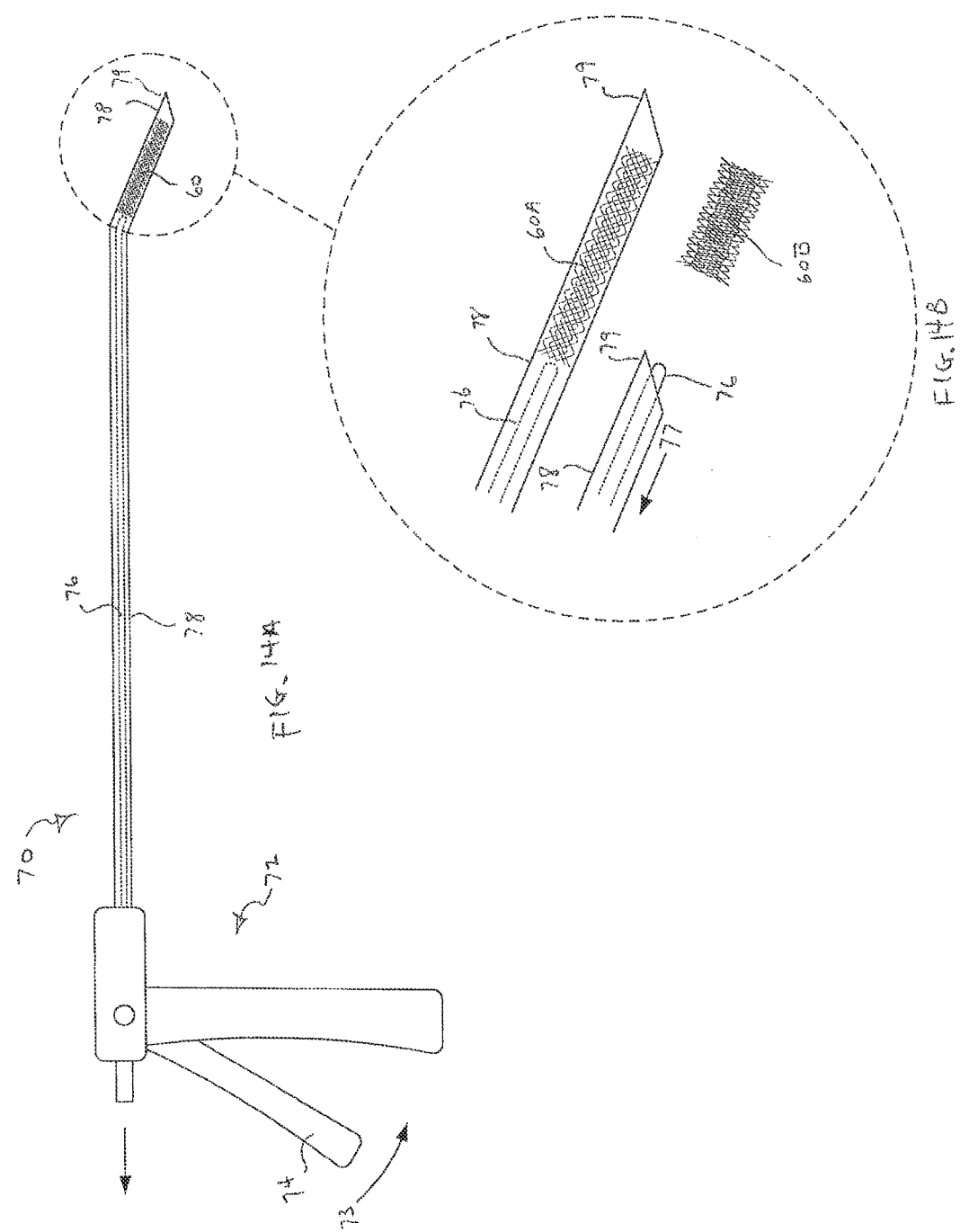

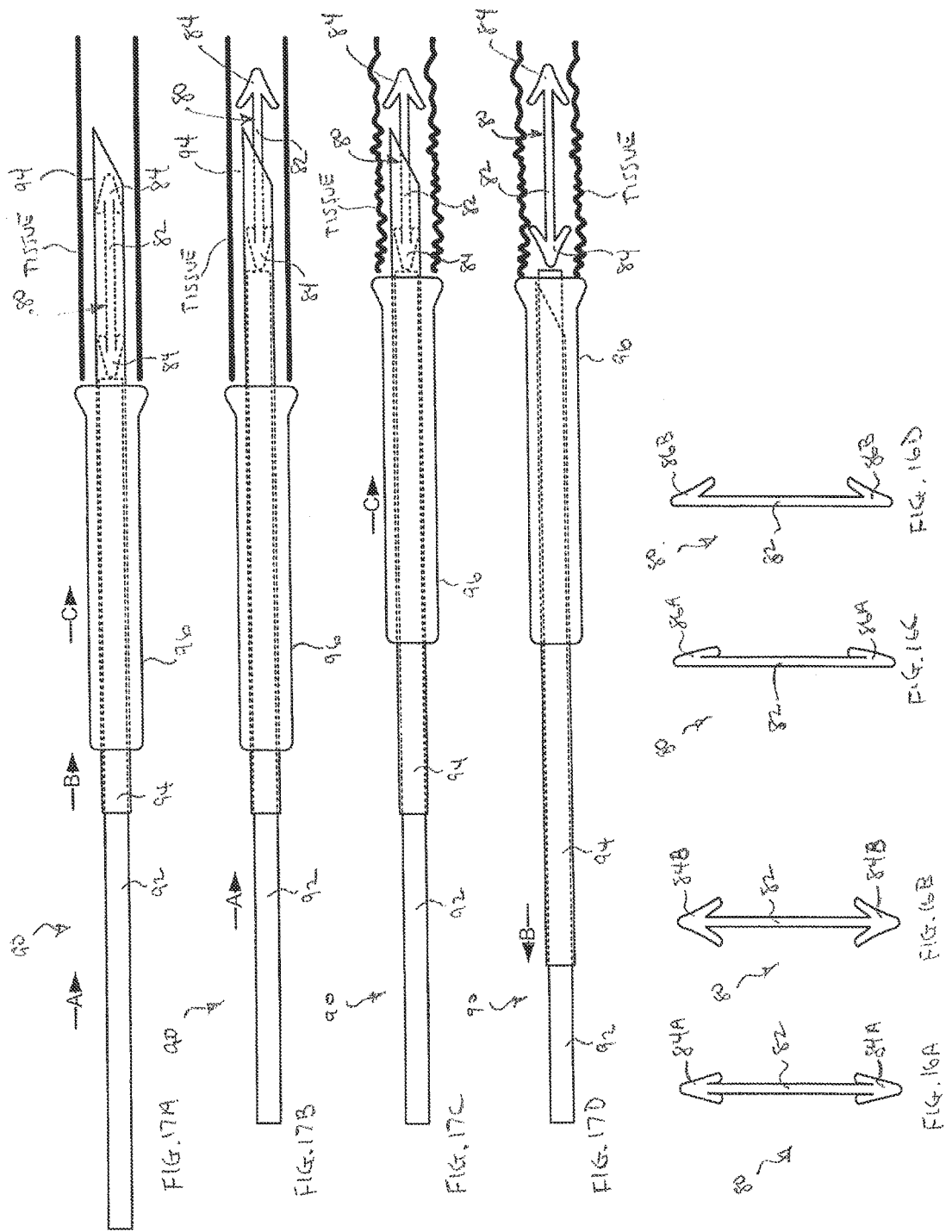

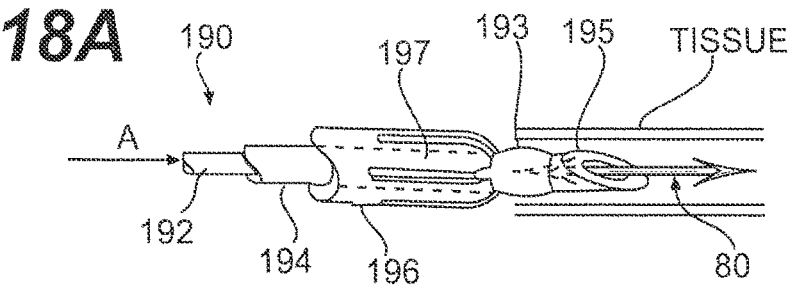
FIG. 18A
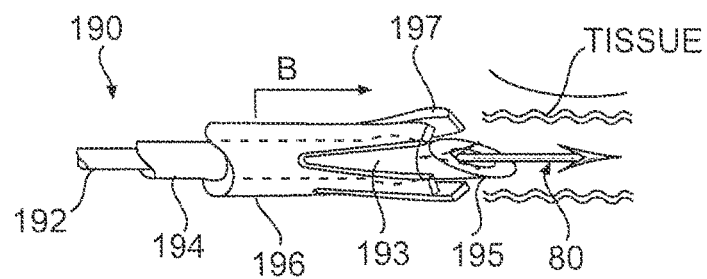
FIG. 18B
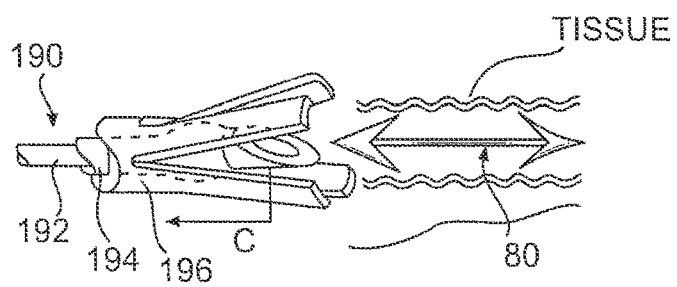
FIG. 18C
FIG. 18D
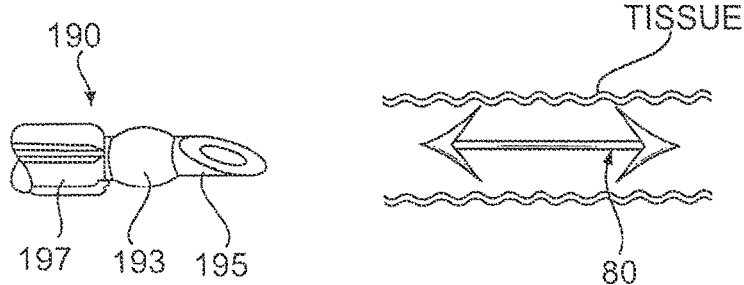

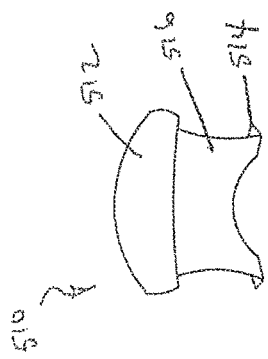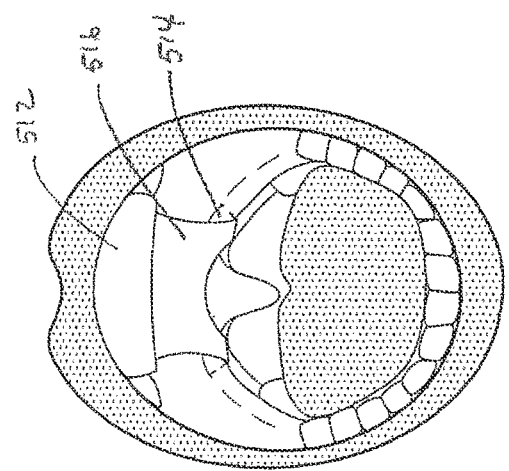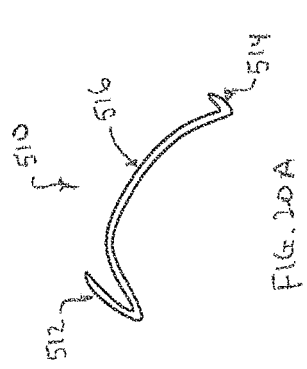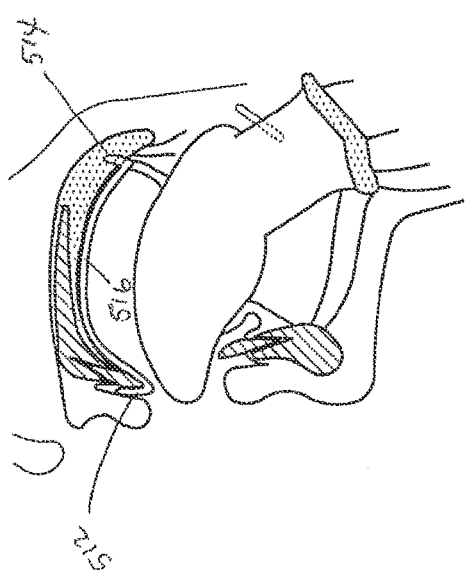

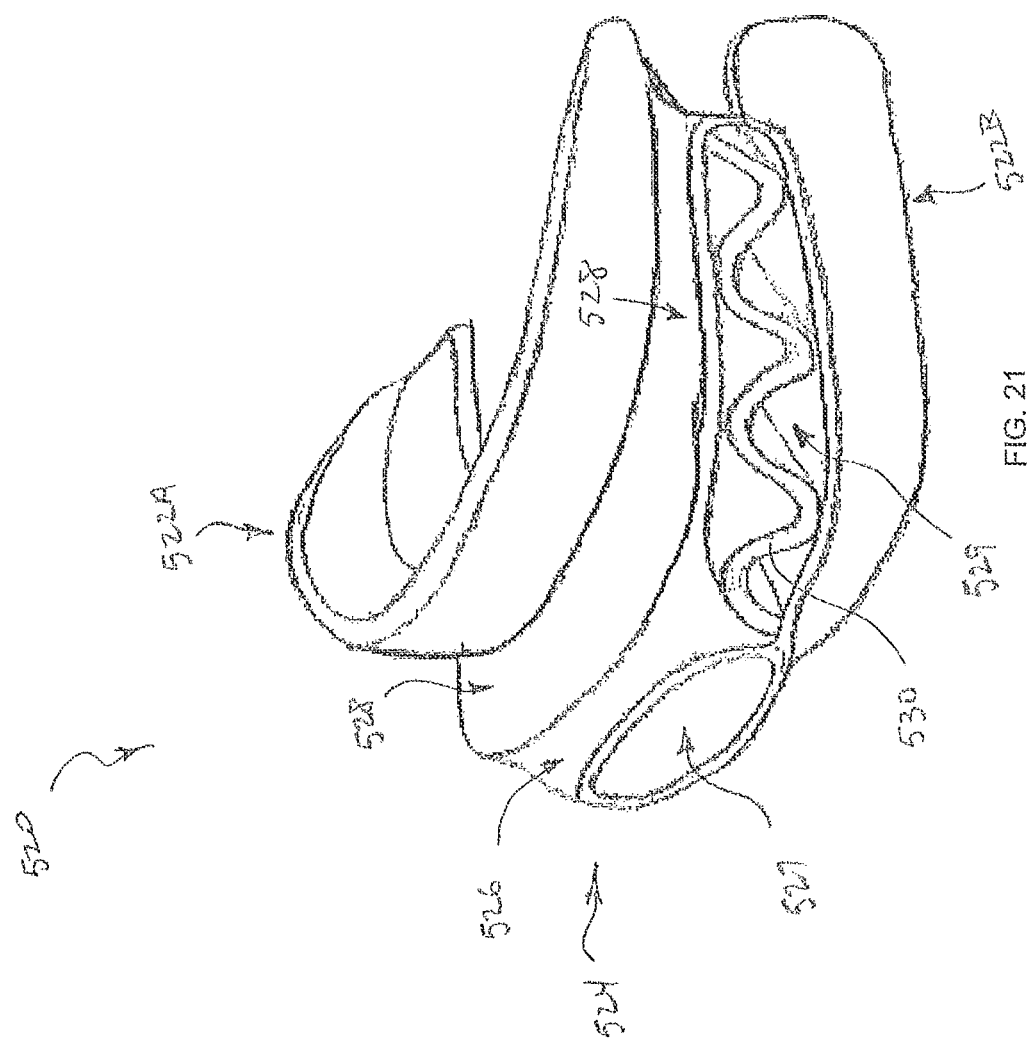

DEVICES AND METHODS FOR SLEEP APNEA TREATMENT

CROSS REFERENCE TO RELATED APPLICATIONS

This application is a divisional of U.S. patent application Ser. No. 14/937,482, filed Nov. 10, 2015, now U.S. Pat. No. 9,757,564, issued Sep. 12, 2017, which is a continuation of U.S. patent application Ser. No. 13/633,670, filed Oct. 2, 2012, now U.S. Pat. No. 9,205,262, issued Dec. 8, 2017, which claims the benefit of and priority to U.S. Provisional Patent Application No. 61/542,617, filed Oct. 3, 2011. This application is related to U.S. patent application Ser. No. 13/113,524, filed May 23, 2011, now abandoned, and also to U.S. patent application Ser. No. 13/106,460, filed May 12, 2011, now U.S. Pat. No. 9,913,982, issued Mar. 13, 2018. The entire disclosures of all of the foregoing applications are incorporated herein by reference.

FIELD OF THE INVENTION

The embodiments described herein relate, for example, to devices and methods for modifying tissue of the upper airway for the treat of obstructive sleep apnea and snoring.

BACKGROUND OF THE INVENTION

Hypoglossal nerve stimulation has been proposed for the treatment of obstructive sleep apnea. An example of an implantable hypoglossal nerve stimulation system is described in U.S. Pat. No. 7,809,442 to Bolea et al. Published data suggest that response to hypoglossal nerve stimulation varies across subjects. It would be desirable to consider adjunct therapies to hypoglossal nerve stimulation to improve outcomes thereof.

SUMMARY OF THE INVENTION

To address this and other unmet needs, the present disclosure provides, by way of example, not limitation, embodiments of devices and methods for treating OSA and snoring by modifying pharyngeal tissue of the upper airway such as, e.g., the palatoglossus, palatopharyngeus, pharyngeoepiglottis, and/or lateral walls. The methods described herein may be performed as an adjunct therapy or as a stand-alone procedure. For example, the methods disclosed herein may be combined with interventions targeting the tongue such as, e.g., hypoglossal nerve stimulation, genioglossus-advancement surgery, implantable devices that advance the tongue, mandibular advancement surgery, mandibular advancement oral appliances, etc.

Embodiments of the present disclosure improve the mechanical coupling between the tongue, the soft palate and the lateral walls and/or improve the mechanical properties of the connective structures. This may be accomplished, for example, by shortening or stiffening the palatoglossal arch, palatopharyngeal arch, pharyngoepiglottic fold, and/or lateral walls while retaining the integrity and function of the structures.

BRIEF DESCRIPTION OF THE DRAWINGS

It is to be understood that both the foregoing summary and the following detailed description are given by way of example, not limitation. Together with the following detailed description, the drawings illustrate example embodiments and serve to explain certain principles. In the drawings.

FIG. 3 is a schematic illustration showing the structures of the upper airway from the oral cavity;

FIG. 4 is a schematic illustration showing isolated structures of the upper airway in a transverse section;

FIGS. 11A-11B are schematic illustrations of a tool for use in the method shown in FIGS. 10A-10B;

FIGS. 12A-12B are schematic illustrations of a method for shortening pharyngeal tissue using an implant device;

FIGS. 13A-13G are schematic illustrations of implant devices for use in the method shown in FIGS. 12A-12B;

FIGS. 14A-14B are schematic illustrations of a tool for use in the method shown in FIGS. 12A-12B;

FIGS. 16A-16D are schematic illustrations of implant devices for use in the method shown in FIGS. 15A-15B;

FIGS. 17A-17D are schematic illustrations of a tool for use in the method shown in FIGS. 15A-15B;

FIGS. 18A-18D are schematic illustrations of an alternative tool for use in the method shown in FIGS. 15A-15B;

FIGS. 20A-20D are schematic illustrations of a palatal device; and

FIG. 21 is a schematic illustration of an oral device.

DETAILED DESCRIPTION OF EXAMPLE EMBODIMENTS

The following detailed description should be read with reference to the drawings in which similar elements in different drawings are numbered the same. The drawings, which are not necessarily to scale, depict illustrative embodiments and are not intended to limit the scope of the present disclosure.

Figure 1:
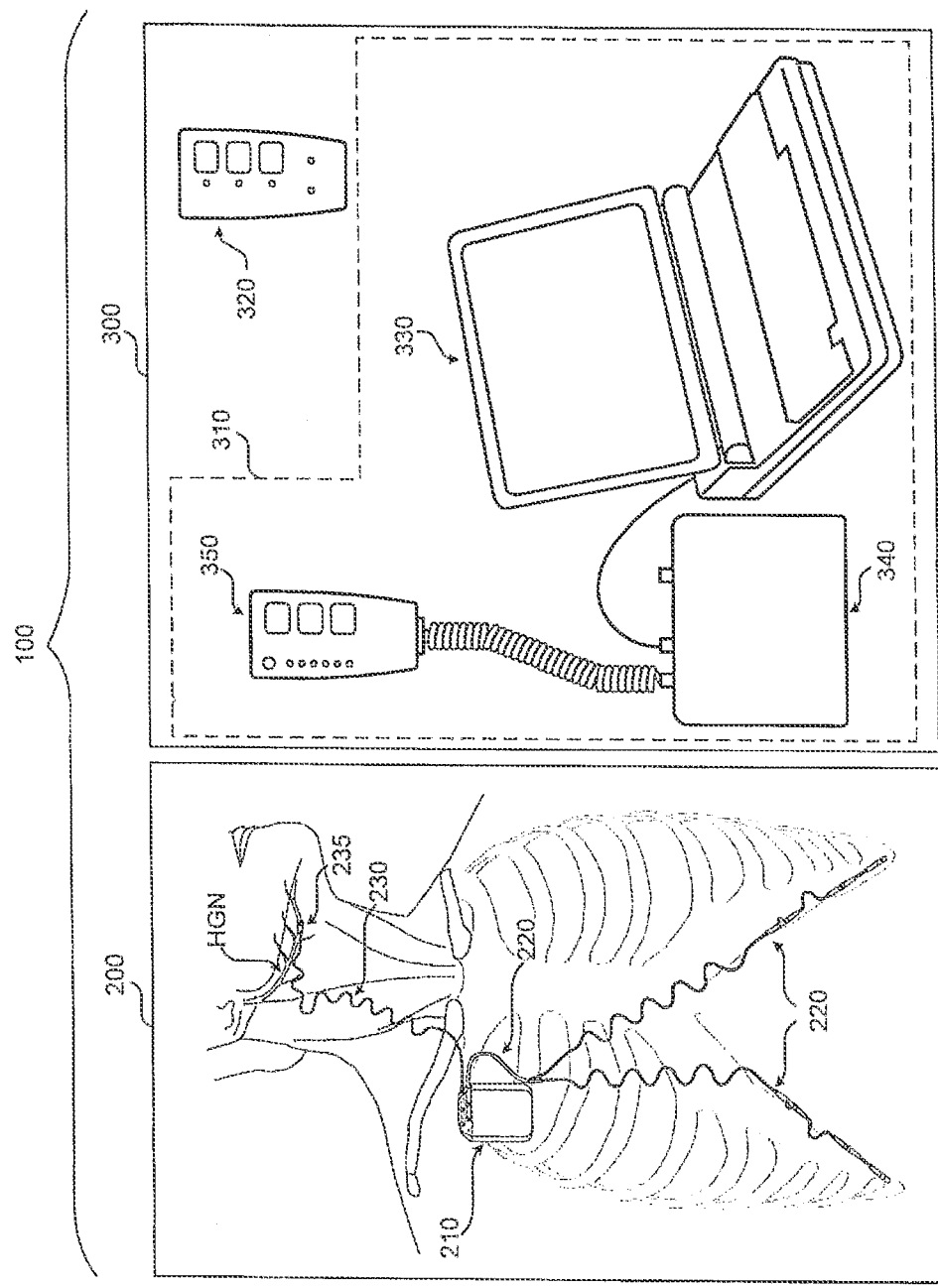
FIG. 1 is a schematic illustration of a hypoglossal nerve stimulation system.
Figure 2:
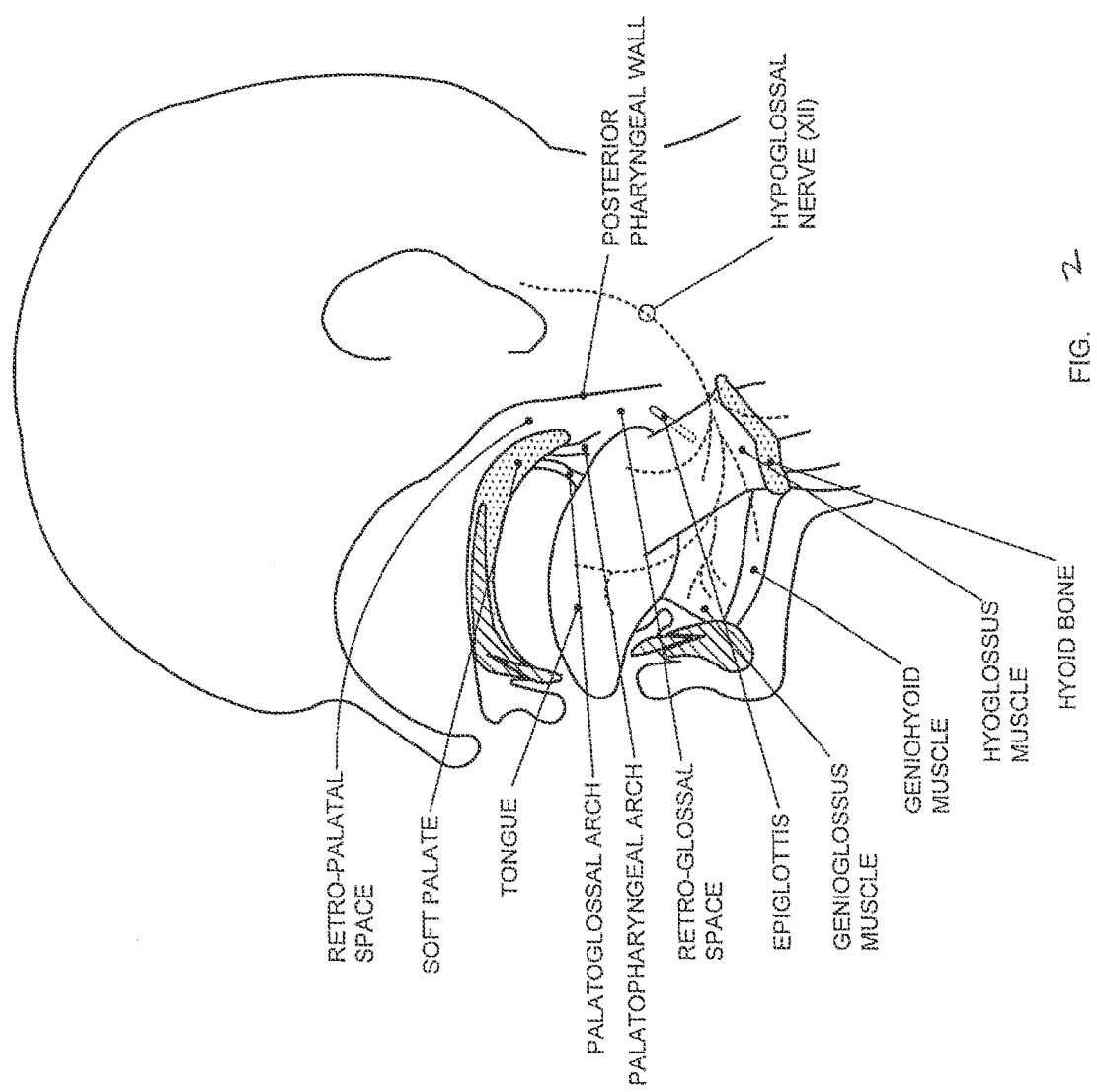
FIG. 2 is a schematic illustration showing the structures of the upper airway in a lateral dissection with the palate and mandible shown in medial sagittal section.

FIG. 1 schematically illustrates an exemplary hypoglossal nerve stimulation (HGNS) system 100 comprising internal components 200 and external components 300. The HGNS system 100 is intended to treat obstructive sleep apnea (OSA) by increasing neuromuscular activity of the genioglossus muscle via stimulation of the hypoglossal nerve (HGN) synchronous with inspiration to mitigate upper airway collapse during sleep. Stimulation is generated by an implantable neurostimulator (INS) 210, synchronized with inspiration as measured by the respiration sensing lead (RSL) 220 using bio-impedance, and delivered to the hypoglossal nerve by a stimulation lead (STL) 230. Alternatively, stimulation may be delivered without respect to respiration, negating the need for respiration sensing capability. A programmer system 310 and a therapy controller 320 are wirelessly linked to the INS 210. The programmer system 310 includes a computer 330, a programmer interface 340, and a programmer head 350. The programmer system 310 is used by the physician to control and program the INS 210 during surgery and therapy titration, and the therapy controller 320 is used by the patient to control limited aspects of therapy delivery (e.g., start, stop, and pause).

The implanted components 200 of the HGNS system 100 include the INS 210, STL 230, and RSL 320. The INS is designed to accommodate one STL 230 and one RSL 220. One STL 230 may be used for unilateral implantation and unilateral hypoglossal nerve stimulation. Similarly, one RSL 220 may be used for respiration detection, and may be bifurcated as shown.

The implanted components 200 may be surgically implanted with the patient under general anesthesia. The INS 210 may be implanted in a subcutaneous pocket inferior to the clavicle over the pectoralis fascia. The distal end of the STL 230 (cuff 235) may be implanted on the hypoglossal nerve or a branch of the hypoglossal nerve in the submandibular region, and the proximal end of the STL 230 may be tunneled under the skin to the INS 210. The RSL 220 may be tunneled under the skin from the INS 210 to the rib cage and placed on both lateral sides of the costal margin. The INS 210 detects respiration via the RSL 220 using bio-impedance and stimulates the hypoglossal nerve via the STL 230 synchronous with inspiration.

Further aspects of the HGNS system 100 may be found in U.S. patent application Ser. No. 13/106,460, filed May 12, 2011, entitled OBSTRUCTIVE SLEEP APNEA TREATMENT DEVICES, SYSTEMS AND METHODS to Bolea et al., the entire disclosure of which is incorporated herein by reference.

Activation of the genioglossus muscle by HGNS causes anterior displacement of the tongue, thus opening the retro-glossal airway. Activation of the genioglossus muscle can also cause anterior displacement of the soft palate, thus opening the retro-palatal airway space. Activation of the genioglossus muscle can further cause lateral displacement of the lateral pharyngeal walls, thus further opening the upper airway. In this manner, activation of the genioglossus muscle by HGNS can mitigate different levels and modes of upper airway collapse in OSA subjects.

Although the effect of genioglossus activation on the tongue to open the retro-glossal airway is predictable given the mechanism of action, the effect of genioglossus activation on the soft palate and lateral walls has been heretofore poorly understood and variable across subjects. Nevertheless, in the majority of OSA patients, the soft palate and the lateral walls can contribute to upper airway collapse, alone or in combination with the tongue. Thus, to the extent that activation of the genioglossus by HGNS does not fully mitigate upper airway collapse in a given subject, adjunct therapies as described herein may be considered to address other levels and modes of upper airway collapse, thus potentially improving the subject's overall response to therapy.

The present disclosure provides a number of different therapies that may be used adjunctively with another OSA therapy such as therapies targeting the tongue (e.g., hypoglossal nerve stimulation, genioglossus-advancement, mandibular advancement surgery, mandibular advancement oral appliances, etc.). Alternatively, the therapies described herein may be used as a stand-alone therapy for OSA and/or snoring. To better understand the function of the therapies described herein, it is helpful to consider the anatomical structures of the upper airway and the interactions of those structures.

With reference to FIGS. 2-6, the anatomical linkages between the tongue, soft palate and lateral walls may be explained in more detail. With specific reference to FIG. 2, the hypoglossal nerve (cranial nerve XII) innervates the genioglossus muscle, which is the largest upper airway dilator muscle. Activation of the genioglossus muscle via stimulation of the hypoglossal nerve causes tongue protrusion and anterior displacement of the soft palate, due to linkage via the palatoglossal arch (muscle). Anterior displacement of the soft palate, in turn, can cause tension to be applied to the lateral pharyngeal walls via the palatopharyngeal arch (muscle). Thus, activation of the genioglossus muscle causes opening of the upper airway at the level of the tongue base (retro-glossal space), at the level of the soft palate (retro-palatal space) via the palatoglossal arch, and along the lateral walls via the palatopharyngeal arch.

The anatomical linkage between the tongue base (genioglossus) and the soft palate via the palatoglossal arch, and the anatomical linkage between the soft palate and the lateral walls via the palatopharyngeal arch may be more clearly seen in FIGS. 3 and 4. The palatoglossus muscle forms the palatoglossal arch and the anterior-inferior aspect of the soft palate on either side of the uvula. The inferior and lateral ends of the palatoglossus muscle insert into the genioglossus muscle. Posterior to the palatoglossal arch are the palatine tonsils, and posterior to the palatine tonsils is the palatopharyngeus muscle forming the palatopharyngeal arch and the posterior-inferior aspect of the soft palate on either side of the uvula. The inferior and lateral ends of the palatopharyngeus muscle insert into the lateral walls of the pharynx.

Figure 5:
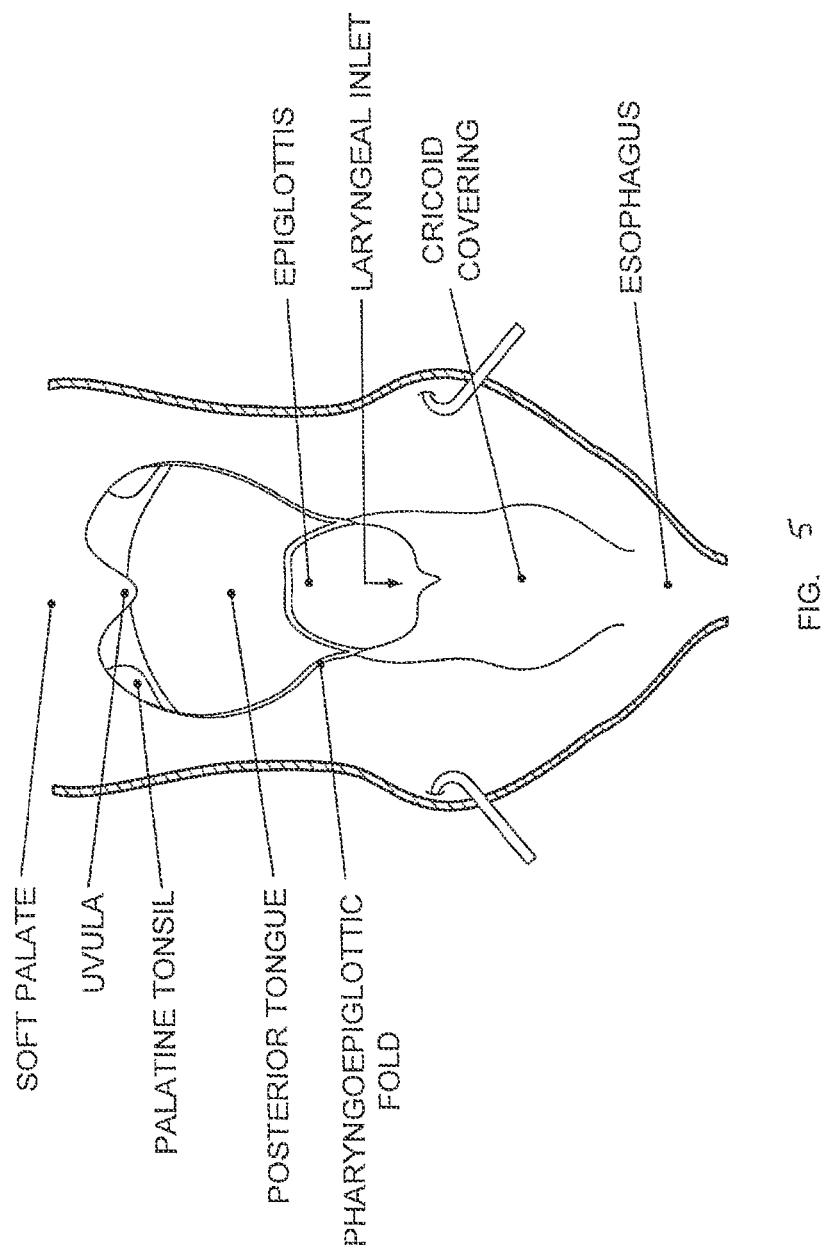
FIG. 5 is a schematic illustration showing structures of the upper airway in a posterior dissection of the interior pharynx.

The inferior anatomical linkage between the soft palate and the lateral walls via the pharyngoepiglottic fold may be more clearly seen in FIG. 5. Activation of the genioglossus serves to pull the soft palate anteriorly via the palatoglossal linkage. Anterior displacement of the soft palate serves to apply anterior and lateral (outward) tension to the lateral pharyngeal walls via the palatopharyngeal linkage as well as the inferior lateral pharyngeal walls via the pharyngoepiglottic linkage.

Figure 6:
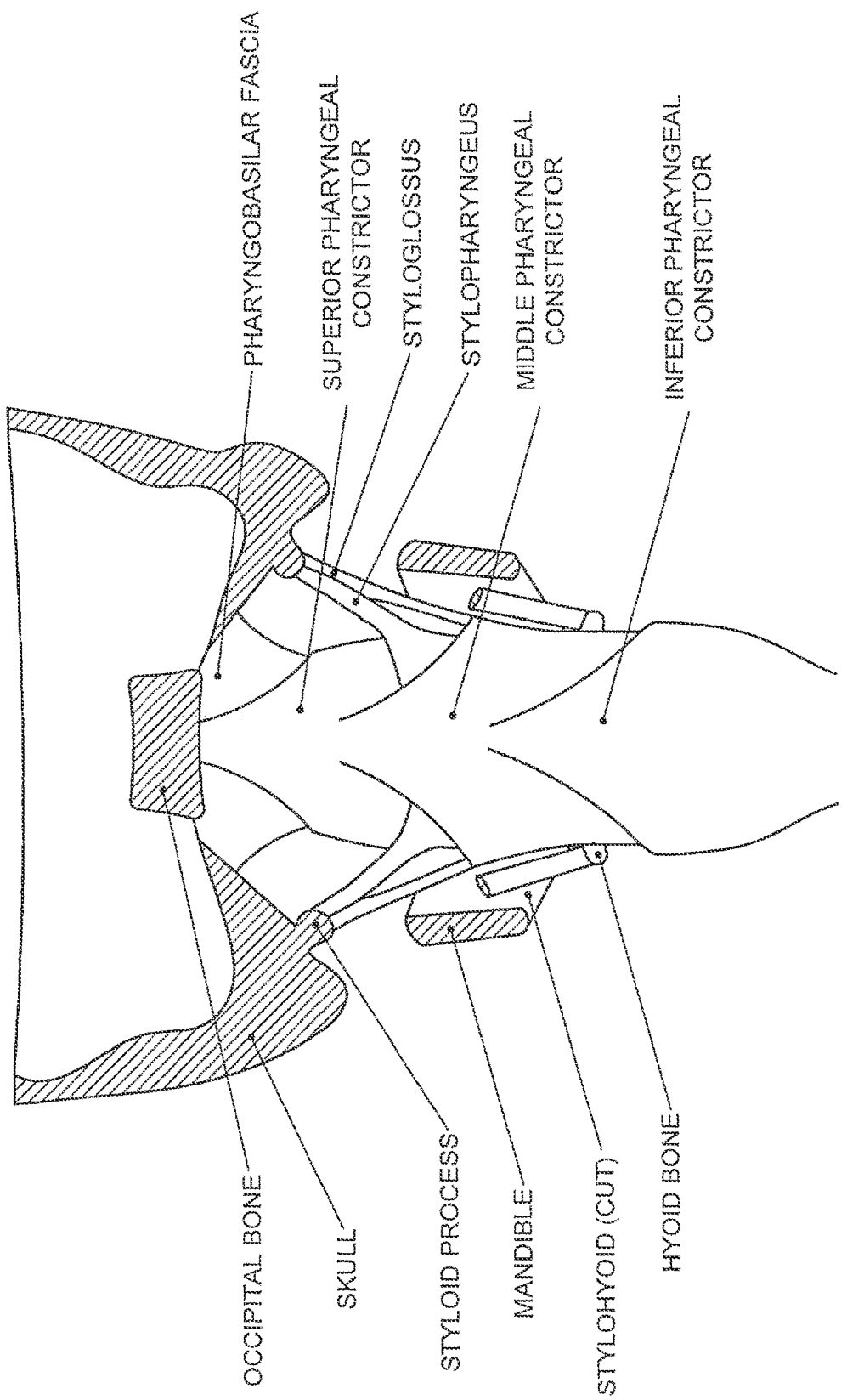
FIG. 6 is a schematic illustration showing structures of the upper airway in a posterior dissection of the exterior pharynx.

The anatomical linkage between the tongue base (genioglossus) and the lateral pharyngeal walls may be better appreciated with reference to FIG. 6. The anterior-inferior aspect (not visible) of the styloglossus muscles insert into the genioglossus, and the posterior-superior aspect of the styloglossus muscles attach to the styloid process. Similarly, the anterior-inferior aspect (not visible) of the stylopharyngeus muscles insert into the lateral pharyngeal walls, and the posterior-superior aspect of the stylopharyngeus muscles attach to the styloid process. The glossopharyngeal aspects of the superior pharyngeal constrictor muscle also insert into the genioglossus. Thus, activation of the genioglossus serves to apply tension to the styloglossus and the glossopharyngeal aspects of the superior pharyngeal constrictor muscle, which in turn apply lateral outward tension to the lateral pharyngeal walls by virtue of the lateral outward position of the styloid process and the linkage via the stylopharyngeus muscles.

The integrity and extent of the aforementioned linkages may vary across subjects, and thus their response to HGNS therapy may vary accordingly. These linkages are significant because most people who snore or have OSA will have some retro-palatal collapse with involvement of the palate and/or lateral walls. In these subjects, retro-palatal collapse may be due to poor linkage (i.e., poor coupling) between the genioglossus and soft palate, the soft palate and lateral walls, and/or the tongue and lateral walls, possibly the result of tissue redundancy (i.e., slack) in the palatoglossus, palatopharyngeus, and/or pharyngoepiglottic fold, respectively. Tissue redundancy may also be present in the lateral pharyngeal walls due to adipose tissue (i.e., fat) at discrete locations (e.g., fat pads) or distributed throughout the pharyngeal walls, particularly in patients with high BMI, which is common in OSA sufferers.

By modifying these connective structures using the devices and methods described herein, the tendency of the tongue, soft palate, and/or lateral walls to collapse may be mitigated as an adjunct to HGNS therapy or as a stand-alone therapy to treat OSA and/or snoring. The connective structures may be modified using the devices and methods described herein by changing their configuration and/or dimension (e.g., shortening their length) and/or changing their mechanical properties (e.g., increasing their stiffness), for example. Although some embodiments are described with reference to a specific pharyngeal structure (e.g., palatoglossal tissue), the same embodiment may be applied to other pharyngeal structures (e.g., palatopharyngeal tissue) in the alternative or in combination.

Figure 7A:
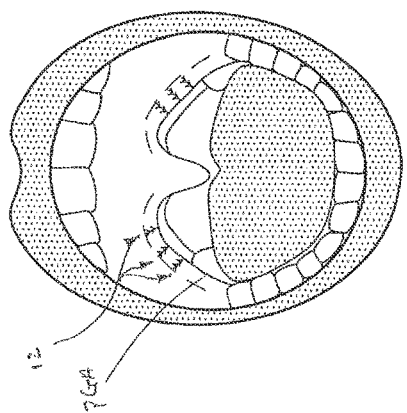
FIGS. 7A-7F, 8A-8B, 9, and 10A-10B are schematic illustrations of methods for shortening pharyngeal tissue.
Figure 7B:
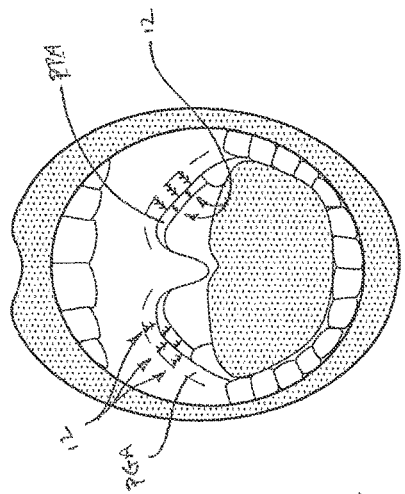

With reference to FIGS. 7A-7B, a method of shortening the palatoglossal arch (PGA) is shown schematically. As seen in FIG. 7A, tissue is removed (cut or ablated) from the PGA to form a void 10 limited to the palatoglossal muscle and surrounding mucosa while leaving the rest of the soft palate unchanged. The amount and shape of the tissue removed may vary, to correspond to the amount of PGA shortening desired. In this example, a triangular notch 10 is formed symmetrically on both sides of the PGA. Subsequently, the notches 10 are surgically closed with sutures 12 or the like to bring the cut edges into approximation and thereby shorten the length of the PGA an amount approximately equal to the sum of the bases of the triangular notches as seen in FIG. 7B. A triangular notch may be beneficial because it removes more tissue from the inferior aspect of the PGA (base of triangle) while minimizing tissue removal from the superior aspect of the PGA (apex of triangle), thus enabling shortening of the PGA while minimizing disruption of the remainder of the soft palate. Thus shortening the length of the PGA applies tension to the soft palate and moves it anteriorly relative to the tongue, thereby mitigating retro-palatal collapse (OSA) and tissue vibration (snoring). Any resultant scarring may serve to stiffen the respective tissue structures thus enhancing the effect.

Figure 7C:
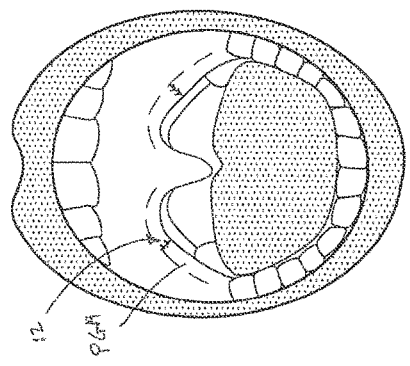
Figure 7E:
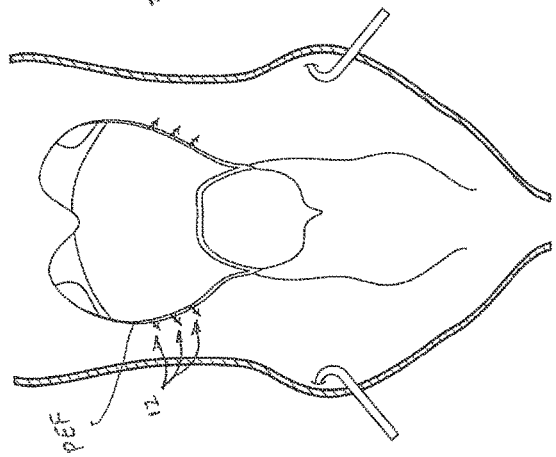
Figure 7D:
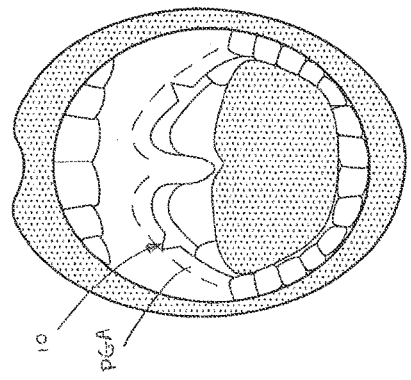
Figure 7F:
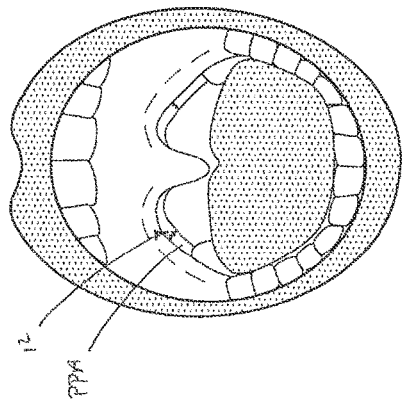

As an alternative, a plurality of tissue sections may be removed and closed from both sides of the PGA as shown in FIG. 7C. In addition, although described with reference to the PGA, the same technique may be applied to other pharyngeal connective structures either alone or in combination. For example, the same technique may be applied to the palatopharyngeal arch (PPA) as shown in FIG. 7D and/or the pharyngoepiglottic fold (PEF) as shown in FIG. 7E. Also by way of example, this technique may be applied to a combination of pharyngeal structures such as the PGA and PPA as shown in FIG. 7F.

Figure 8B:
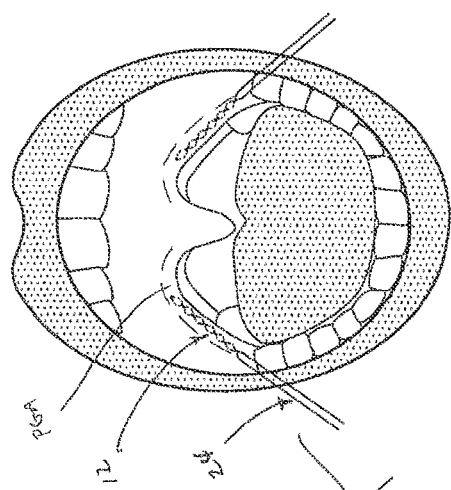
Figure 8A:
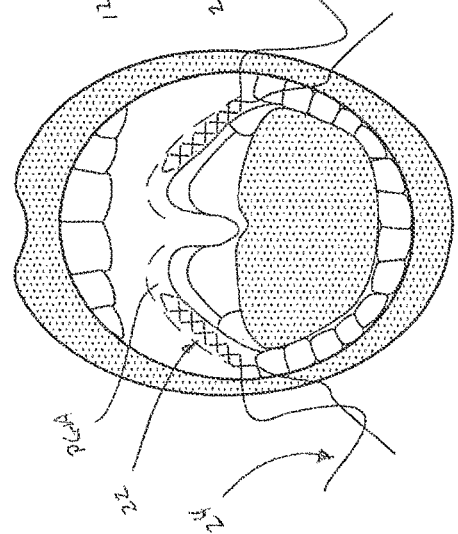

With reference to FIGS. 8A-8B, an alternative method of shortening and/or stiffening the palatoglossal arch (PGA) is shown schematically. As seen in FIG. 8A, sutures 22 are bilaterally placed in the PGA in a crisscross fashion. The sutures 22 may generally follow the arcuate shape of the PGA and its width may be limited to the width of the palatoglossal muscle and surrounding mucosa while leaving the rest of the soft palate unchanged. Once in place, the tags ends 24 of the sutures 22 may be pulled relative to the PGA as shown in FIG. 8B to cinch the adjacent tissue length-wise to thereby shorten the length of the PGA and/or stiffen the PGA. Optionally, tissue may be removed from the PGA prior to placement of the sutures 22 as described with reference to FIG. 7A and elsewhere herein. The method described with reference to FIGS. 8A-8B may be applied to other pharyngeal structures in the alternative or in combination.

Figure 9:
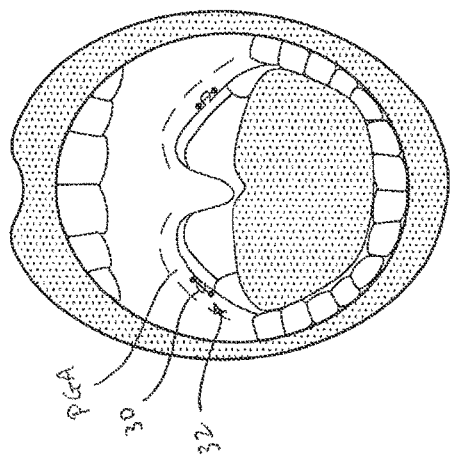

In some instances, it may be desirable to temporarily shorten or stiffen pharyngeal connective structures to determine if there is a positive effect (in terms of mitigating OSA and/or snoring) before performing any of the permanent procedures described herein. To this end, and with reference to FIG. 9, placations 30 may be formed bilaterally in the PGA to shorten its length, and temporary holding devices 32 may be placed across the placations 30 to retain the foreshortened length. Optionally, more than one placation 30 and holding device 32 may be placed on each side of the PGA to adjust the foreshortened length thereof. The holding device 32 may comprise, for example, a stud with a removable end, similar to what is used for body piercing, such as an earring. With the PGA temporarily held in a foreshortened length, the effect thereof may be studied while the patient is awake (e.g., by awake nasoendoscopy) and/or while the patient is asleep (e.g., drug induced sleep endoscopy and/or, polysomnography). If a beneficial result (e.g., enlarged airway, improved coupling, reduced snoring, and/or reduction in apneas and hypopneas) is observed in any of such studies, the temporary holding device 32 may be removed and a permanent procedure as described herein may be performed to have the same foreshortening and/or stiffening effect on the PGA. The method described with reference to FIG. 9 may be applied to other pharyngeal structures in the alternative or in combination.

Figure 10B:
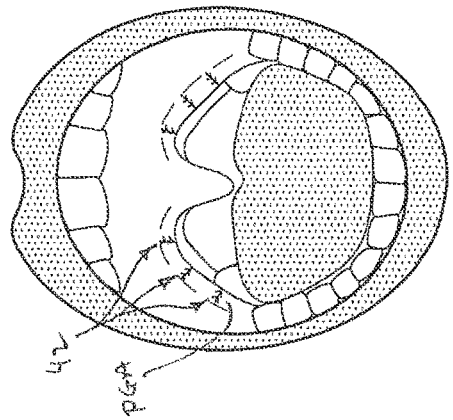
Figure 10A:
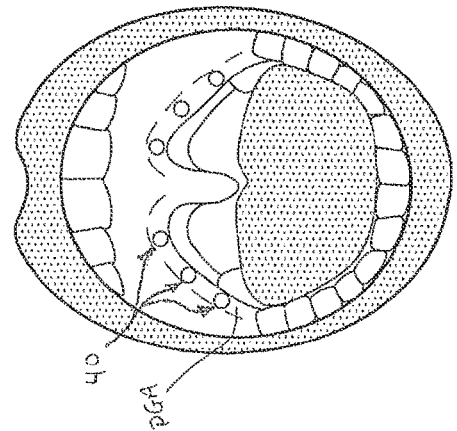

With reference to FIGS. 10A-10B, an alternative method of shortening the palatoglossal arch (PGA) is shown schematically. As seen in FIG. 10A, tissue is removed (cut or ablated) from the PGA to form a circular void 40 between the inferior and superior aspects of the PGA while leaving the rest of the soft palate unchanged. The amount (diameter) removed may vary, to correspond to the amount of PGA shortening desired. In this example, several circular holes are formed symmetrically on both sides of the PGA. Subsequently, the holes 40 are surgically closed with sutures 42 or the like to bring the cut edges into approximation and thereby shorten the length of the PGA an amount approximately equal to the sum of the diameters of the circular holes as seen in FIG. 10B. A circular (or other shape) hole may be beneficial because it is confined to the PGA between the inferior and superior aspects of the PGA. The method described with reference to FIGS. 10A-10B may be applied to other pharyngeal structures in the alternative or in combination.

With reference to FIGS. 11A and 11B, a punch tool 50 is shown which may be used to form the holes 40 shown in FIG. 10A. Punch tool 50 includes a handle 52 with an actuation lever 54 to advance a tubular punch 56 through outer tube 57 to engage die 58. When lever 54 is squeezed relative to handle 52, the punch 56 is advanced in outer tube 57. With die 58 fixed relative to outer tube 57, advancement of the punch 56 as indicated by arrow 51 causes the distal cutting edge of the punch 56 to press against the facing surface of the die 58. The tool 50 may be positioned in the oral cavity with the PGA disposed between the distal cutting edge of the punch 56 and the facing surface of the die 58. When so positioned, the lever 54 may be actuated to advance the die, pinch the PGA tissue between the punch 56 and die 58, and form a hole of any desired shape therein. This step may be repeated for each additional hole to be formed in the PGA or other desired pharyngeal tissue structure.

With reference to FIGS. 12A-12B, an alternative method of shortening and/or stiffening the palatoglossal arch (PGA) is shown schematically. As seen in FIG. 12A, an insertion tool 70 may be used to implant devices 60 bilaterally below the mucosa or in the muscle of the PGA as shown in FIG. 12B. The implant device 60 may comprise an elastic structure having an elongated delivery configuration 60A and a foreshortened deployed configuration 60B as shown in FIGS. 13A and 13B, respectively. The implant device 60 may comprise, for example, braided metal (e.g., stainless steel or super elastic nickel titanium alloy) or braided elastomer (e.g., silicone) formed in a tubular shape, with an elongated state 60A and a relaxed state 60B. Thus, when implant device 60 is implanted submucosally in the PGA, the device 60 expands diametrically to engage the surrounding tissue, and shortens longitudinally to stiffen and/or shorten the length on the PGA. Multiple implant devices 60 may be implanted in the PGA, and this method may be applied to other pharyngeal structures in the alternative or in combination.

An alternative implant device 160 is shown in FIGS. 13C-13G. In this embodiment, implant device 160 includes a shaft portion 162 and two anchors 164. The implant device 160 is placed into pharyngeal tissue in a first elongated state 160A as shown in FIG. 13C, and subsequently assumes a second foreshortened state 160B as shown in FIG. 13D. To change from the elongated state to the foreshortened state, a length changing core 166 may be disposed in the shaft portion 162, with access thereto provided by a plurality of slots 163 in the shaft portion 162 as shown in FIG. 13E. The length changing member 166 may comprise a bio-resorbable material, a heat-shrink polymer that shortens upon application of heat, or a dissolvable material that dissolves upon exposure to a solvent (e.g., saline). The shaft portion 162 and anchors 164 may comprise an elastic polymer material such as silicone. Initially, the shaft portion 162 is stretched lengthwise and the core 166 is disposed therein to hold the shaft portion 162 in a stretched or elongated state. Post implantation, the core 166 shortens (by resorbing, dissolving, or exposure to heat) causing the shaft portion 162 to shorten as it returns to its relaxed state. As the shaft 162 shortens, the anchors 164 engage the surrounding tissue causing the tissue to foreshorten and stiffen. The anchors may comprise tines 164 as shown in FIG. 13E, a mesh 164' as shown in FIG. 13F, or a porous material 164" as shown in FIG. 13G, wherein the mesh 164' and the porous material 164" promote tissue ingrowth for anchoring purposes.

To facilitate insertion of the implant device 60 or 160 under the mucosa or in the muscle of the PGA, an insertion tool 70 may be used as shown in FIGS. 14A and 14B. Insertion tool 70 includes a handle 72 having a lever 74 that may be squeezed as indicated by arrow 73. The lever 74 is mechanically coupled to a flexible outer tube 78, which is retractable relative to an inner member 76 that is fixed relative to handle 72. The outer tube 78 includes a sharpened tip 79 for penetrating into the mucosa and a distal opening for release of the device 60. The distal end of the inner member 76 abuts the proximal end of implant device 60. The outer tube 78 retains the implant device 60 in an elongated, reduced diameter, delivery configuration 60A. When the distal sharpened end of the outer tube 78 is placed under the mucosa or in the muscle of the PGA, the outer tube 78 may be retracted as indicated by arrow 77 by actuation of lever 74 as indicated by arrow 73, thereby releasing the implant device 60 in a shortened, increased diameter, deployed configuration 60B. Thus, the device 60 expands from an elongated delivery configuration 60A to a shortened deployed configuration 60B, thereby stiffening and/or shortening the length of the PGA. The insertion tool 70 may be used to delivery implant device 60 or 160 to other pharyngeal structures in the alternative or in combination.

Figure 15B:
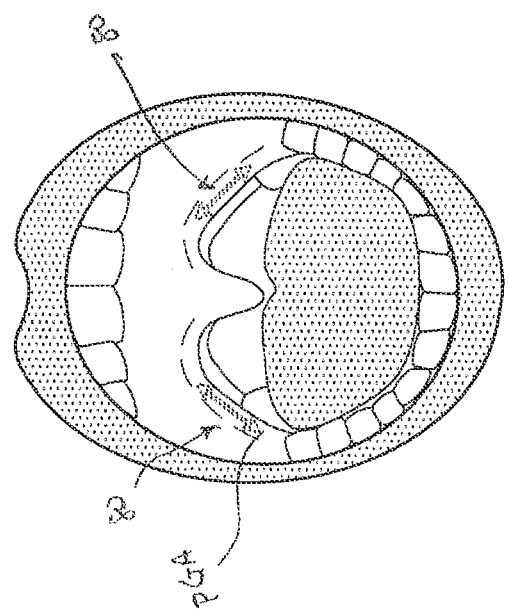
FIGS. 15A-15B are schematic illustrations of an alternative method for shortening pharyngeal tissue using an implant device.
Figure 15A:
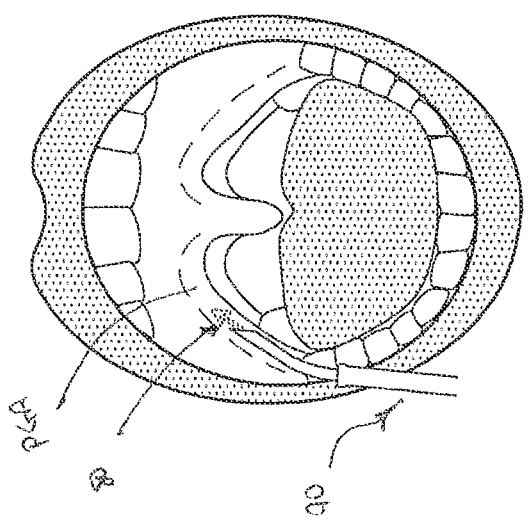

With reference to FIGS. 15A-15B, an alternative method of shortening and/or stiffening the palatoglossal arch (PGA) is shown schematically. As seen in FIG. 15A, an insertion tool 90 may be used to implant devices 80 bilaterally below the mucosa or in the muscle of the PGA as shown in FIG. 15B. Prior to full insertion of the implant devices 80 in the PGA, the PGA tissues are foreshortened using the insertion device 90, for example, such that the implant devices 80 hold the PGA in a foreshortened state. The implant device 80 may comprise a semi-flexible structure that can flex laterally but resists elongation axially. As shown in FIGS. 16A and 16B, the implant device 80 may include a shaft portion 82 with double-barbed anchors 84 at opposite ends of the shaft portion 82. Alternatively, as shown in FIGS. 16C and 16D, the implant device 80 may include a shaft portion 82 with single-barbed anchors 86 at opposite ends of the shaft portion 82. Anchors 84 and 86 may have a low profile delivery configuration 84A and 86A, and an expanded deployed configuration 84B and 86B, as shown. The anchors 84 and 86 are unidirectional such that they can be easily inserted into tissue in one direction but resist withdraw in the other (opposite) direction. For each implant device 80, the unidirectional characteristic of each anchor is opposite, such that the anchor 84/86 on a first end of the shaft 82 is unidirectional in a first direction, and the anchor 84/86 on the second end of the shaft 82 is unidirectional in a second direction opposite from the first direction. This arrangement of the anchors 84/86 allows tissues surrounding the implant device 80 to foreshorten along the shaft portion 82 while holding the tissues in a foreshortened state to shorten the length of the PGA. The implant device 80 may comprise, for example, an implantable grade permanent polymer, a bio-resorbable polymer (e.g., PLLA, PGA), etc. Multiple implant devices 80 may be implanted in the PGA, and this method may be applied to other pharyngeal structures in the alternative or in combination.

To facilitate insertion of the implant device 80 under the mucosa or in the muscle of the PGA, an insertion tool 90 may be used as shown in FIGS. 17A-17D. Insertion tool 90 includes an inner push member 92, an outer push tube 96, and an intermediate tube 94 with a sharpened distal end. Initially, the intermediate tube 94 extends distally beyond the inner push member 92 and the outer push tube 96, with the implant device 80 contained in tube 94 in a delivery configuration with the anchors 84 folded in. In this configuration, all components 92, 94, 96 of the insertion tool 90 are advanced distally in unison as indicated by arrows A, B, C, and the intermediate tube 94 is inserted into the tissue as shown in FIG. 17A. Once the intermediate tube 94 containing the implant device 80 is advanced sufficiently into the target tissue, the inner push member 92 is advanced distally as shown by arrow A, while the intermediate tube 94 and outer tube 96 remain stationary, thus pushing the implant device 80 out of the distal end of the intermediate tube 94 to deploy distal anchor 84 as shown in FIG. 17B. The outer push tube 96 is advanced distally as shown by arrow C, while the inner push member 92 and the intermediate tube 94 remain stationary, thus engaging the distal flared end of the outer tube 96 against the target tissue causing it to foreshorten as shown in FIG. 17C. The intermediate tube 94 is then withdrawn proximally as shown by arrow B, while the inner push member 92 and outer push tube 96 remain stationary, thus deploying the proximal anchor 84 of the implant device 80 to hold the tissue in a foreshortened state as shown in FIG. 17D. The insertion tool 90 may be used to delivery device 80 to other pharyngeal structures in the alternative or in combination.

An alternative insertion tool 190 may be used to facilitate insertion of the implant device 80 under the mucosa or in the muscle of the PGA as shown in FIGS. 18A-18D. Insertion tool 190 includes an inner push member 192, an outer push tube 196, and an intermediate tube 194. The intermediate tube 194 includes a sharpened tip 195 and a bulb portion 193 having an enlarged diameter. The outer tube 196 includes a slotted distal end defining a plurality of finger-like projections 197 that extend outward when advanced over the bulb portion 193 of the intermediate tube 194. Initially, the intermediate tube 194 extends distally beyond the inner push member 192 and the outer push tube 196, with the implant device 80 contained in the intermediate tube 194 in a delivery configuration with the anchors folded in. In this configuration, all components 192, 194, 196 of the insertion tool 190 are advanced distally in unison, and the intermediate tube 194 is inserted into the tissue. Once the intermediate tube 194 containing the implant device 80 is advanced sufficiently into the target tissue, the inner push member 192 is advanced distally as shown by arrow A, while the intermediate tube 194 and outer tube 196 remain stationary, thus pushing the implant device 80 out of the distal end of the intermediate tube 194 to deploy the distal anchor of the implant device 80 as shown in FIG. 18A. The outer push tube 196 is advanced distally as shown by arrow B, while the inner push member 192 and the intermediate tube 194 remain stationary, thus engaging the finger-like projections 197 of the outer tube 196 against the bulb portion 193 of the intermediate tube 194 and causing the fingers to flare outward. The flared projections 197 then push against the target tissue causing it to foreshorten as shown in FIG. 18B. The intermediate tube 194 is then withdrawn proximally as shown by arrow C, while the inner push member 192 and outer push tube 196 remain stationary, thus deploying the proximal anchor of the implant device 80 to hold the tissue in a foreshortened state as shown in FIG. 18C. The insertion tool 190 may then be removed from the target tissue leaving the implant device in place as shown in FIG. 18D. The insertion tool 190 may be used to delivery device 80 to other pharyngeal structures in the alternative or in combination.

Figure 19A:
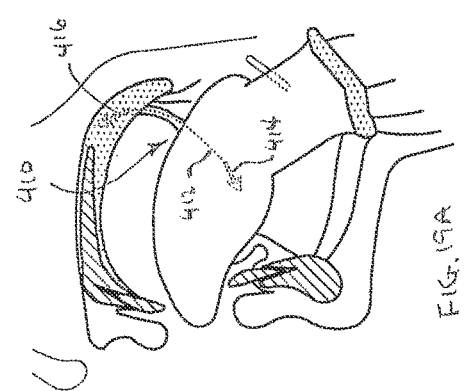
FIGS. 19A-19F are schematic illustrations of alternative methods for shortening pharyngeal tissue using implant devices.
Figure 19B:
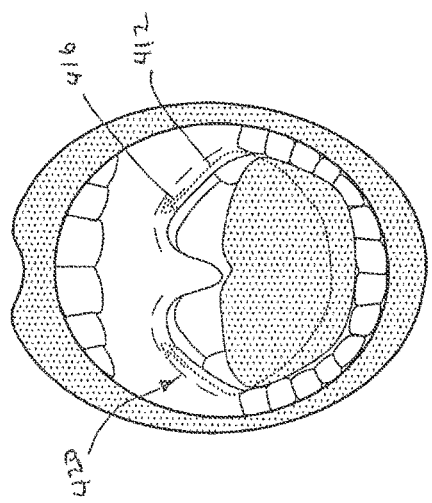
Figure 19C:
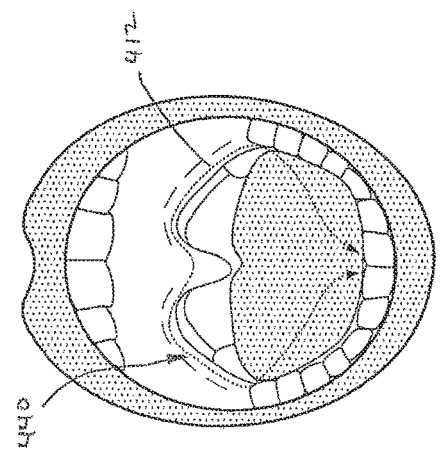

With reference to FIGS. 19A-19F, various implant devices are shown schematically which, in general, improve coupling between the tongue and the soft palate via the palatoglossal arch. In FIGS. 19A and 19B, two implant devices 410 extend from the soft palate, through the palatoglossal arch and into the genioglossus. Each implant device 410 includes a tether member 412 (e.g., multi-filament polymer), and two tissue anchors (e.g., polymer barb) 414 and 416 residing in the genioglossus and soft palate, respectively. The implant devices 410 may be implanted using insertion tool 90 for example, such that it applies tension between the soft palate and tongue via the palatoglossal arch, thereby improving coupling therebetween. In FIG. 19C, a variation of implant device 410 is shown as implant device 420, which functions in a similar manner but eliminates tissue anchors in the tongue in favor a loop of the tether 412.

Figure 19D:
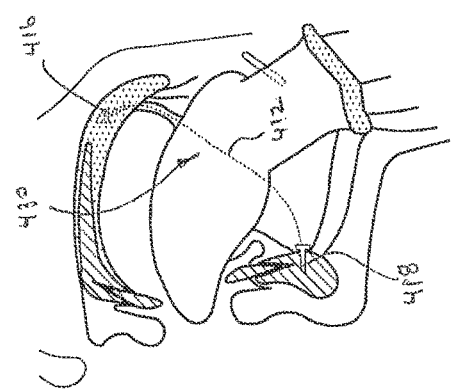
Figure 19E:
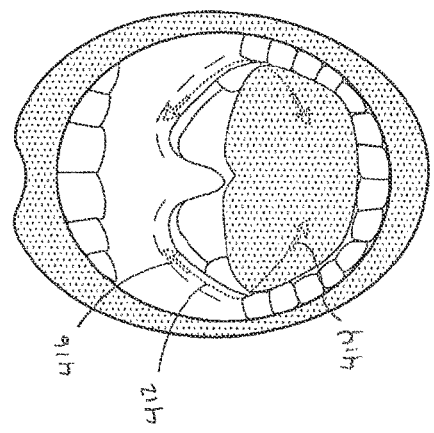
Figure 19F:
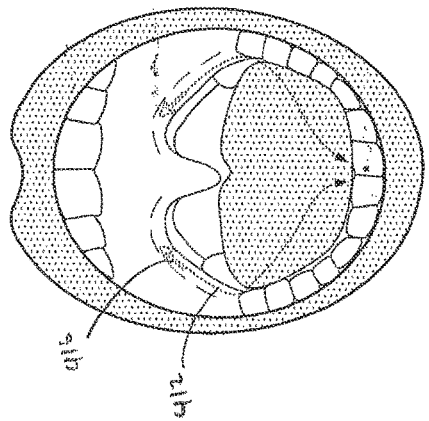

In FIGS. 19D-19E, two implant devices 430 extend from the soft palate, through the palatoglossal arch and genioglossus, to the mandible. In this embodiment, device 430 includes a tether member 412, a tissue anchor 416 residing in the soft palate, and a bone anchor 418 residing in the mandible. The implant devices 430 may be implanted using insertion tool 90 for example, such that it applies tension between the soft palate and tongue via the palatoglossal arch, thereby improving coupling therebetween. In FIG. 19F, a variation of implant device 430 is shown as implant device 440, which functions in a similar manner but eliminates tissue anchors in the palate in favor a loop of the tether 412.

With reference to FIGS. 20A-20D, a palatal appliance 510 is shown schematically. As seen in the side view shown in FIG. 20A and the front view shown in FIG. 20B, the palatal appliance 510 includes a dentition portion 512, a palatal portion 514, and a connecting arch member 516. As shown in FIGS. 20C and 20D, the dentition portion 512 engages the front teeth, the palatal portion 514 includes two tabs that engage the posterior aspect of the soft palate on either side of the uvula, and the arch member 516 extends along the roof of the mouth to connect the dentition portion 512 to the palatal portion 514. The palatal appliance 510 may be formed of conventional materials used for dental appliances, and may be customized for an individual patient using a boil-and-bite technique or a mold-and-thermoform technique. In use, the palatal appliance 510 keeps the soft palate from falling posteriorly, and may be under-sized to displace the soft palate anteriorly from its normal position. Palatal appliance 510 may be used as a stand-alone therapy in the case of isolated retro-palatal collapse, or used as an adjunct to HGNS therapy in the case of poor palatal coupling.

With reference to FIG. 21, an oral appliance 520 is shown schematically. The oral appliance 520 includes upper and lower dentition portions 522A and 522B, and a spacer portion 524. The dentition portions 522A and 522B engage the teeth, and the spacer 524 resides between the upper and lower teeth as well as the upper and lower lips. An arch member (not shown) may be provided to extend from the spacer along the roof of the mouth. The spacer portion 524 includes a middle portion 526 and two lateral portions 528. The middle portion 526 defines a lumen 527 through which air may flow freely, or into which the tongue may extend (if used in conjunction with HGNS therapy). Similarly, the lateral portions 528 define lumens 529 through which air may flow freely. The lateral portions 528 may include baffles 530 in a serpentine shape, for example, to provide structural support while permitting airflow therethrough. The arch portion (not shown) may also include a flow path in communication with lumens 527 and 529 through which air may flow freely. The dentition portions 522A and 522B secure the appliance 520 in the mouth during sleep, but permits easy insertion and removal of the appliance 520 to/from the oral cavity at the beginning and ending of the sleep period, respectively. Optionally, one dentition portion 522A or 522B may be used. The spacer 524 keeps the mouth open (teeth and lips) to permit mouth breathing, despite the tendency of the mouth to close during sleep. Similarly, the arch portion maintains a flow path for mouth breathing, despite the tendency of the tongue to fall against the roof of the mouth during sleep. The spacer 524 may have a rectangular housing with a serpentine support baffle 530 as shown, or the serpentine support structure 530 without a housing. The oral appliance 520 may be formed of conventional materials used for dental appliances, and may be customized for an individual patient using a boil-and-bite technique or a mold-and-thermoform technique. In use, the oral appliance 520 maintains an open flow path for mouth breathing, despite the tendency of the mouth to close and the tongue to rest against the roof of the mouth during sleep. Oral appliance 520 may be used as a stand-alone therapy in the case of isolated retro-palatal collapse, or used as an adjunct to HGNS therapy in the case of poor palatal coupling.

The adjunct devices and therapies described herein may be used in combination with HGNS therapy, or other therapeutic interventions that directly address retro-glossal collapse. For example, the adjunct therapies described herein may be used in combination with genioglossus advancement surgery, mandibular advancement surgery, mandibular advancement (oral) appliances, etc. Alternatively, the therapies described herein may be used as stand-alone procedures to treat OSA and/or snoring.

Examples of conventional OSA therapies that may be used as an adjunct to HGNS include palate surgeries such as uvulopalatopharyngoplasty (UPPP), palatopharyngoplasty, uvulopalatal flap, and palatal implants (e.g., Pillar® implants sold by Medtronic). Palate surgeries primarily affect upper airway collapse at the level of the palate. As such, these therapies may be considered as adjunct to HGNS in subjects that have residual retro-palatal collapse with HGNS therapy, possibly due to poor anatomical coupling between the tongue and the palate.

From the foregoing, it will be apparent to those skilled in the art that the present disclosure provides, in non-limiting embodiments, devices and methods for treating OSA and snoring by modifying pharyngeal tissue of the upper airway such as, e.g., the palatoglossus, palatopharyngeus, pharyngeoepiglottis, and/or lateral walls. Further, those skilled in the art will recognize that the present disclosure may be manifested in a variety of forms other than the specific embodiments described and contemplated herein. Accordingly, departures in form and detail may be made without departing from the scope and spirit of the present disclosure as described in the appended claims.

What is claimed is:

1. A method of treating an upper airway condition of a patient, the method comprising:
   implanting a stimulation device in the patient, the stimulation device configured to deliver an electrical stimulation signal to the patient's hypoglossal nerve to induce a first movement of the patient's upper airway tissue having a first magnitude corresponding to a first efficacy in treating the upper airway condition of the patient; and
   implanting a fixation device in the patient's upper airway tissue, the fixation device having a first end secured to a first portion of upper airway tissue coupled to the tongue of the patient and an opposing second end secured to a second portion of upper airway tissue coupled to at least one of the patient's soft palate, palatopharyngeus, or palatoglossus,
   wherein the implanting of the fixation device modifies the first movement to define a second movement of the patient's upper airway tissue having a second magnitude greater than the first magnitude, the second magnitude corresponding to a second efficacy in treating the upper airway condition of the patient.

2. The method of claim 1, wherein the upper airway condition is an obstructive sleep apnea condition of the patient, and wherein at least one of the first and second movements mitigates the obstructive sleep apnea condition.

3. The method of claim 1, wherein the upper airway condition includes a first tissue collapse at a first location within the patient's upper airway and a second tissue collapse at a second location within the patient's upper airway, wherein the first movement corresponds to a mitigation of the first tissue collapse, and wherein the second movement corresponds to a mitigation of both the first tissue collapse and the second tissue collapse.

4. The method of claim 1, wherein the second movement includes a tightening of the patient's pharyngeal tissue.

5. The method of claim 4, wherein the second movement includes a shortening of the patient's palatoglossus.

6. The method of claim 4, wherein the second movement includes a shortening of the patient's palatopharyngeus.

7. The method of claim 4, wherein the second movement includes a shortening of the patient's pharyngoepiglottic fold.

8. The method of claim 1, wherein the first movement includes a contraction of the patient's genioglossus.

9. The method of claim 1, the method further comprising implanting a sensing lead in the patient, wherein the stimulation device is further configured to sense inspirations of the patient via the sensing lead and deliver the electrical stimulation signal synchronized with the sensed inspirations of the patient.

10. The method of claim 1, wherein the stimulation device is further configured to modify the electrical stimulation signal in response to receiving a signal from an external therapy controller.

11. A system for treating an upper airway condition of a patient, the system comprising:
    a stimulation device configured to deliver an electrical stimulation signal to the patient's hypoglossal nerve to induce a first movement of the patient's upper airway tissue having a first magnitude corresponding to a first efficacy in treating the upper airway condition of the patient; and
    a fixation device configured for implantation in the patient's upper airway tissue, the fixation device having a first end configured to be secured to a first portion of upper airway tissue coupled to the tongue of the patient and an opposing second end configured to be secured to a second portion of upper airway tissue coupled to at least one of the patient's soft palate, palatopharyngeus, or palatoglossus,
    wherein the implantation of the fixation device modifies the first movement to define a second movement of the patient's upper airway tissue having a second magnitude greater than the first magnitude, the second magnitude corresponding to a second efficacy in treating the upper airway condition of the patient.

12. The system of claim 11, wherein the upper airway condition is an obstructive sleep apnea condition of the patient, and wherein at least one of the first and second movements mitigates the obstructive sleep apnea condition.

13. The system of claim 11, wherein the upper airway condition includes a first tissue collapse at a first location within the patient's upper airway and a second tissue collapse at a second location within the patient's upper airway, wherein the first movement corresponds to a mitigation of the first tissue collapse, and wherein the second movement corresponds to a mitigation of both the first tissue collapse and the second tissue collapse.

14. The system of claim 11, wherein the second movement includes a tightening of the patient's pharyngeal tissue.

15. The system of claim 14, wherein the second movement includes a shortening of the patient's palatoglossus.

16. The system of claim 14, wherein the second movement includes a shortening of the patient's palatopharyngeus.

17. The system of claim 14, wherein the second movement includes a shortening of the patient's pharyngoepiglottic fold.

18. The system of claim 11, wherein the first movement includes a contraction of the patient's genioglossus.

19. The system of claim 11, the system further comprising a sensing lead, wherein the stimulation device is further configured to sense inspirations of the patient via the sensing lead and deliver the electrical stimulation signal synchronized with the sensed inspirations of the patient.

20. The system of claim 11, the system further comprising an external therapy controller, wherein the stimulation device is further configured to modify the electrical stimulation signal in response to receiving a signal from the external therapy controller.

* * * * *